(12) United States Patent
Salcudean et al.

(10) Patent No.: US 7,731,661 B2
(45) Date of Patent: Jun. 8, 2010

(54) METHOD FOR IMAGING THE MECHANICAL PROPERTIES OF TISSUE

(75) Inventors: Septimiu E. Salcudean, Vancouver (CA); Robert N. Rohling, Vancouver (CA); Emre Turgay, Vancouver (CA)

(73) Assignee: The University of British Columbia, Vancouver (CA)

( * ) Notice: Subject to any disclaimer, the term of this patent is extended or adjusted under 35 U.S.C. 154(b) by 1339 days.

(21) Appl. No.: 10/963,795

(22) Filed: Oct. 14, 2004

(65) Prior Publication Data
US 2005/0119568 A1 Jun. 2, 2005

Related U.S. Application Data

(60) Provisional application No. 60/510,528, filed on Oct. 14, 2003.

(30) Foreign Application Priority Data
Feb. 11, 2004 (CA) .................................. 2457376

(51) Int. Cl.
*A61B 8/00* (2006.01)
(52) U.S. Cl. ................. 600/437; 600/407; 600/427; 600/443; 600/561; 367/92; 367/94; 367/103; 367/189
(58) Field of Classification Search ................. 600/407, 600/301, 443, 427, 437, 561; 367/92, 94, 367/103, 189
See application file for complete search history.

(56) References Cited

U.S. PATENT DOCUMENTS 4,771,792 A * 9/1988 Seale .................... 600/587

| | | | |
|---|---|---|---|
| 5,086,775 A | 2/1992 | Parker et al. | |
| 5,099,848 A | 3/1992 | Parker et al. | |
| 5,107,837 A | 4/1992 | Ophir et al. | |
| 5,178,147 A | 1/1993 | Ophir et al. | |
| 5,293,870 A | 3/1994 | Ophir et al. | |
| 5,474,070 A | 12/1995 | Ophir et al. | |
| 5,606,971 A | 3/1997 | Sarvazyan | |

(Continued)

OTHER PUBLICATIONS

Tissue Elasticity Reconstruction Based on 3-D FEM. Makoto Yamakawa and Tsuyoshi Shiina. May 1999. Japanese Journal of Applied Physics. http://jjap.ipap.jp/link?JJAP/38/3393/pdf.*

(Continued)

*Primary Examiner*—Brian Casler
*Assistant Examiner*—Joel M Lamprecht
(74) *Attorney, Agent, or Firm*—Oyen Wiggs Green & Mutala LLP

(57) ABSTRACT

An imaging system comprises a device to excite mechanical waves in elastic tissue, a device for measuring the resulting tissue motion at a plurality of locations interior to the tissue at a number of time instances, a computing device to calculate the mechanical properties of tissue from the measurements, and a display to show the properties according to their location. A parameter identification method for calculating the mechanical properties is based on fitting a lumped dynamic parametric model of the tissue dynamics to their measurements. Alternatively, the mechanical properties are calculated from transfer functions computed from measurements at adjacent locations in the tissue. The excitation can be produced by mechanical vibrators, medical needles or structures supporting the patient. The measurements may be performed by a conventional ultrasound imaging system and the resulting properties displayed as semi-transparent overlays on the ultrasound images.

34 Claims, 17 Drawing Sheets

U.S. PATENT DOCUMENTS

| | | | |
|---|---|---|---|
| 5,839,441 A | 11/1998 | Steinberg | |
| 5,860,934 A * | 1/1999 | Sarvazyan | 600/587 |
| 5,903,516 A | 5/1999 | Greenleaf et al. | |
| 5,904,651 A * | 5/1999 | Swanson et al. | 600/407 |
| 5,919,139 A | 7/1999 | Lin | |
| 5,991,239 A | 11/1999 | Fatemi-Booshehri | |
| 6,068,597 A | 5/2000 | Lin | |
| 6,161,031 A * | 12/2000 | Hochman et al. | 600/407 |
| 6,176,827 B1 | 1/2001 | Cohen-Bacrie et al. | |
| 6,270,459 B1 | 8/2001 | Konofagou et al. | |
| 6,371,912 B1 | 4/2002 | Nightingale et al. | |
| 6,438,401 B1 * | 8/2002 | Cheng et al. | 600/407 |
| 6,486,669 B1 | 11/2002 | Sinkus et al. | |
| 6,508,768 B1 | 1/2003 | Hall et al. | |
| 6,514,204 B2 | 2/2003 | Alam et al. | |
| 6,520,913 B1 * | 2/2003 | Pesavento et al. | 600/438 |
| 6,558,324 B1 | 5/2003 | Von Behren et al. | |
| 6,860,855 B2 * | 3/2005 | Shelby et al. | 600/459 |
| 6,878,115 B2 * | 4/2005 | Dione et al. | 600/459 |
| 2004/0010222 A1 * | 1/2004 | Nunomura et al. | 604/22 |
| 2006/0052696 A1 * | 3/2006 | Shiina et al. | 600/437 |

OTHER PUBLICATIONS

Tissue Elasticity Reconstruction Based on 3-D Displacement Data Estimated by the Weighted Phase Gradient Method. Shiina Nitta and Ueno. 1999 IEEE Ultrasonics Symposium.*

Ophir, J., et al., Elastography: ultrasonic estimation and imaging of the elastic properties of tissue, J. Eng. Med., 1999, 213:203-233.

Ophir, J., et al., Elastography: ultrasonic imaging of tissue strain and elastic modulus in vivo, Eur. J. Ultrasound, 1996, 3:49-70.

Gao, L., et al., Imaging of the elastic properties of tissue—a review, Ultrason. Med. Biol., 1996, 22(8):959-977.

Fung, Y.C., Biomechanics: Mechanical Properties of Living Tissues, 1993, Springer.

Sinkus, R., et al., High-resolution tensor MR elastography for breast tumour detection, Phys. Med. Biol., 2000, 45.

Viola, F., et al., Imaging viscoelastic properties of the vitreous, IEEE Ultrasonics Symposium, 2001.

Ljung, L., System Identification, Theory for the User, 1999, Prentice-Hall.

* cited by examiner

METHOD FOR IMAGING THE MECHANICAL PROPERTIES OF TISSUE

REFERENCE TO RELATED APPLICATIONS

This application claims the benefit of U.S. Provisional Application No. 60/510,528, filed 14 Oct. 2003.

BACKGROUND OF THE PRESENT INVENTION

1. Field of the Invention

This invention relates to diagnostic imaging in general, and to measurement of the mechanical properties of tissue in particular.

2. Description of the Related Art

The basis of medical imaging is the measurement of a property of tissue that varies with tissue composition. Medical images are formed by displaying intensities as a function of these properties measured at multiple locations in the body. From such images, a depiction of anatomy or pathology is gained. Each different imaging modality in common use, such as X-ray, computed tomography, ultrasound and magnetic resonance imaging, measures a different property of tissue.

Mechanical properties of tissue are important indicators of disease potential. Indeed, palpation techniques are commonly used by medical doctors to determine the potential for disease—for example, stiffer tissue regions that can be felt as harder objects can indicate the presence of breast or liver malignancies. There are a number of in-vivo techniques for measuring mechanical properties of tissue.

Static Elastography is a new medical imaging modality that aims to depict elasticity, a mechanical property of tissue. Elasticity is also referred to as stiffness, or the inverse compliance. The variation of elasticity among tissue types and pathology is well known. A number of journal articles describing the clinical applications of elastography are listed by Hall et al. in U.S. Pat. No. 6,508,768. In fact, elastography can be considered as an extension of the traditional diagnostic technique of palpation—the pressing of tissue to feel for differences in elasticity.

The history and development of elastography is given in the following reviews:

J. Ophir, S. K. Alam, B. Garra, F. Kallel, E. Konofagou, T. Krouskop and T. Varghese, "Elastography: ultrasonic estimation and imaging of the elastic properties of tissue", J. Eng. Med., 213:203-233, 1999.

J. Ophir, I. Cespedes, H. Ponnekanti, and Y. Yazdi, "Elastography: ultrasonic imaging of tissue strain and elastic modulus in vivo", Eur. J. Ultrasound, 3:49-70, 1996.

L. Gao, K. J. Parker, R. M. Lerner and S. F. Levinson, "Imaging of the elastic properties of tissue—a review", Ultrason. Med. Biol., 22(8):959-977, 1996.

Depending on the technique of generating the measured tissue displacement, static elastography methods can be classified as employing global deformation or local deformation.

Measurement of applied global deformation. In static elastography, two images are taken of a region of tissue. One image is taken during compression of the tissue with a nominal static external force. The second image is taken during compression with a higher static external force. The difference between the images is used to calculate relative elasticity. The external force refers to axial pressure applied typically to the surface of the skin above a region of interest. The basic principle is that stiff tissues will compress less than compliant tissues. Dividing each image into small regions and comparing the movement of these regions between the two images provides a quantitative measurement of the local strain. Provided the stress induced from the external force is uniform throughout the tissue, then local elasticity estimates can be made. The underlying assumption is that the strain is linearly related to the stress and that this relationship is described mathematically by a linear scale factor called the Young's modulus, or simply elasticity. Ultrasound is a common imaging modality for this method because it is ubiquitous, non-invasive, safe, inexpensive and portable. Patents of this approach include those by Ophir et al., in U.S. Pat. Nos. 5,107,837, 5,178,147, 5,293,870, 5,474,070, Konofagou et al in U.S. Pat. No. 6,270,459, Alam et al. in U.S. Pat. No. 6,514,204, Steinberg et al. in U.S. Pat. No. 5,839,441, Hall et al. in U.S. Pat. No. 6,508,768, VonBehren et al. in U.S. Pat. No. 6,558,324 and Cohen-Bacrie et al. in U.S. Pat. No. 6,176,827. The differences among these patents are mainly in the construction of the apparatus, the methods to compute strain from the ultrasound data and the display of the results.

Measurement of local deformation in response to focused ultrasound excitation. The second category of static elastography describes methods that excite only a small volume of tissue interior to the body using high intensity focused ultrasonic waves. In Nightingale et al. in U.S. Pat. No. 6,371,912 the high intensity ultrasound produces an acoustic radiation force and is measured with a second set of low-intensity ultrasound images. The high intensity pushing pulses are interleaved with the low intensity imaging pulses to provide more rapid measurements. The relative local displacement is measured at different locations and displayed. The displacements are related to the local elasticity. Tissue dynamics are not captured in the process.

The major disadvantage of all static elastography methods is that they measure only static properties of tissue. In addition, because static elastography uses information at a single frequency (zero Hz or dc), the method is sensitive to noise and measurement bias.

In what we will call dynamic elastography, a force is applied to tissue and the resulting tissue motion is measured, i.e., multiple tissue displacement or velocity measurements are made over a period of time. These measurements can be displayed directly (e.g., measured magnitude of tissue velocity generated by a vibration source) or following some excitation-dependent signal processing (e.g., the quality factor of the tissue velocity frequency response to a vibration source acting at different frequencies).

There are many methods proposed for dynamic elastography. We will classify these broadly into the following four categories, based on whether tissue excitation and measurement is local, and whether there is an underlying tissue model whose parameters are being identified.

We will start by discussing three approaches that do not rely upon fitting the data to a parameterized tissue model.

Velocity response to an external vibration source. The first category of dynamic elastography describes methods that apply mechanical waves globally to a region of tissue using an external vibration source and then measure the resulting tissue motions. The tissue response is usually measured by ultrasound as described in Parker et al. in U.S. Pat. Nos. 5,086,775, 5,099,848, and Lin in U.S. Pat. Nos. 5,919,139, and 6,068,597. Ultrasound is normally used here because Doppler imaging is widely available on commercial ultrasound machines. The Doppler signals measure local velocity and the absence of velocity can indicate the presence of stiff inclusions such as tumors. As an alternative, magnetic resonance imaging offers improvements in image quality, at the expense of speed and cost. See for example, U.S. Pat. No. 6,486,669 described later.

In the methods disclosed in U.S. Pat. Nos. 5,086,775, 5,099,848, 5,919,139, and 6,068,597, the tissue is excited with a vibrator at audio frequencies and the tissue response is measured by power Doppler measurements. In U.S. Pat. Nos. 5,086,775 and 5,099,848, a mechanical exciter sweeps through a range of audio frequencies until a resonant frequency is detected. In U.S. Pat. No. 5,086,775 Doppler shifted signals are analyzed to find the vibration amplitude of a given region of interest. In U.S. Pat. No. 5,099,848, Doppler shifted signals are analyzed to find the vibration amplitude, the discrete eigenmodes, and eigenfrequency of the tissue. These measurements are then converted into other properties such as shear velocity and Q parameter—the quality factor—and displayed. In U.S. Pat. No. 5,919,139, the Doppler shifted signals are analyzed to find the tissue vibration amplitude, the frequency, and the variance. Various combinations of these properties are displayed. In U.S. Pat. No. 6,068,597, the tissue is vibrated with a wide range of frequencies to obtain the full frequency spectrum of the tissue at different locations. Various measurements of the shape of the spectrum around the resonance peak are then displayed.

In all four of these dynamic imaging patents, measurements are made of the velocity and resonance behavior of the tissue, but they are not based on modelling the underlying properties of the tissue, such as the elasticity, viscosity and density that produces the resonance behavior. Moreover, the measurements must be made with an excitation of only one frequency at a time, making the acquisition of data slow.

Tissue response from localized displacements. Sarvazyan in U.S. Pat. No. 5,606,971 uses high-intensity focused ultrasonic waves that are amplitude modulated to generate shear waves at a single location in the tissue. To obtain an image, localized excitations and measurements are repeated at different locations. The shear waves are detected by measuring their amplitude and phase on the surface of the tissue. At least one propagation parameter of the shear waves in the tissue is determined from the phase and amplitude measurements. The parameter can be one of the following group of parameters: shear wave velocity, shear wave attenuation coefficient, amplitude and velocity of shear displacement of tissue particles in the propagating shear wave, spatial an temporal dependencies of these amplitude and velocity of shear displacement of tissue particles. From these calculations, at least one mechanical parameter of tissue is derived, such as shear elasticity modulus, Young's modulus, dynamic shear viscosity, and mechanical impedance. The way the data is analyzed is local in the sense that the calculation of a tissue parameter at a single location is done without considering the effect of the properties of the neighboring tissue regions. This type of analysis is possible because the spatial decay of shear waves is rapid, so neighboring effects are neglected. The requirement that localized shear waves be used constitutes a significant drawback. Only one small region can be excited at a time and the excitation-measurement process must be repeated for multiple regions. This reduces the speed of forming a complete image. And again, the use of high intensity focused ultrasound poses a possible hazard to the patient.

Acoustic emissions from localized displacements. These dynamic elastography methods directly measure the acoustic emissions produced by tissue vibrating as a result of a localized oscillating radiation force. For a constant frequency radiation force, tissues with different viscoelastic properties will produce different emissions. The main idea is to create an oscillating point force in the tissue and measure the emission with a hydrophone. By raster scanning the point source across a region of interest, an image is formed from the magnitude or phase of the measured emissions. The oscillating point force is produced by the intersection of two focused continuous wave ultrasound beams at different frequencies. The interference of the beams at the focal point produces sinusoidal modulation of the ultrasound energy, effectively vibrating the tissue at that point. The use of such systems is called vibro-acoustography. See Greenleaf et al. in U.S. Pat. Nos. 5,903,516 and 5,991,239. The drawbacks of this approach include the need for specialized equipment for both producing the oscillating point force and measuring the emissions. It also does not measure the underlying properties of the tissue, only the resonance behavior. Moreover, it requires raster scanning of a region of interest, instead of allowing simultaneous measurements. This reduces the speed of forming a complete image.

Both localized methods—tissue response and acoustic emissions—produce images of one or more aspects of the tissue response to the dynamic excitations, but do not identify a specific model of the tissue dynamics. Alternatively, the tissue dynamics can be modelled using a parametric model, and the model parameters can be obtained from the measured responses to tissue excitation. The dynamic response of human tissue depends on both the amplitude and the frequency of the excitation (Y. C. Fung, "Biomechanics: Mechanical Properties of Living Tissues", Springer, 1993). Nevertheless, if the amplitude of excitation is small, and frequencies are low, then a linear viscoelastic model can used as a reasonable approximation of the tissue dynamics. We now discuss two approaches that attempt to fit the data to a linear parameteric tissue model.

Parameter identification based on the wave equation and sinusoidal excitation. Sinkus et al. in U.S. Pat. No. 6,486,669 use a mechanical external excitation and magnetic resonance imaging to extract tissue properties from a linear viscoelastic model. This is therefore categorized as having global excitation with model parameter identification. A method is disclosed for vibrating the tissue to create longitudinal mechanical waves with periodic signals, preferably sinusoids, and to obtain the phase and amplitude of the single tone sinusoidal vibrations. To obtain both phase and amplitude, the images and the excitation must be carefully synchronized. From these measurements, they solve the wave equation for the viscoelastic model and calculate the model parameters of elasticity, Poison's ratio, tissue density and attenuation. In particular, the time independent solution of the partial differential wave equations is used. With a time independent approach, the tissue must be excited with a periodic signal, such as one or more toned sinusoids, and an equilibrium must be reached to eliminate the transient responses. Thus, this method is restricted to using excitations with periodic amplitudes to be able to reach equilibrium, and where the ratios of the frequencies is an integer.

The requirement that the excitation consist of carefully controlled frequencies and phases in synchronization with magnetic resonance imaging means that a very complicated system is needed compared to other techniques. Another limitation is the need to reach an equilibrium state before measurements can begin. Since tissue relaxation in response to an excitation may take seconds, the reported times required to obtain an image of parameters is of the order of 30 minutes (R. Sinkus, J. Lorenzen, D. Schrader, M. Lorenzen, M. Dargatz, and D. Holz, "High-resolution tensor MR elastography for breast tumour detection", Phys. Med. Biol. 45, 2000).

Measurement and parameter fit to localized time response to focused ultrasound excitation. In a paper by F. Viola and W. Walker, "Imaging viscoelastic properties of the vitreous", IEEE Ultrasonics Symposium, 2001, focused ultrasound is used to generate a step force in a localized region of tissue.

This tissue region is displaced as a result, and its displacement as a function of time is used to identify the relative stiffness and relative viscosity with which this region is connected to neighboring tissue. This is therefore categorized as having local excitation with model parameter identification. While this method does measure dynamic properties of tissue (relative viscosity), it suffers from a number of drawbacks. First, while focused ultrasound can produce a step force in a small isolated region, this process must be repeated many times at many locations to form a complete image. The speed of the repeated measurements is limited by the need for the tissue to relax from the step force. Viola et al. do not describe a method to speed up the imaging of a larger region and such method is not obvious. Second, the identification technique Viola et al. use to compute relative stiffness and viscosity relies upon the step response of tissue. In essence, a fit to an exponentially decaying tissue region displacement must be obtained. It is well known to experts in parameter identification (see for example L. Ljung, "System Identification, Theory For The User", Prentice Hall, 1999) that such an approach can fail in the presence of noise. Third, in order to obtain dynamic tissue parameters, Viola et al. fit the actual tissue region response to a model using nonlinear optimization techniques. Many iterations may be required for such an approach to produce a set of parameters. Furthermore, there may be local minima.

So in summary, the static elastography methods (both local and global excitation methods) are incapable of measuring the dynamic properties of tissue. The dynamic elastography methods with local excitation have shown an ability to measure some dynamic properties, but the local nature of excitation makes the imaging procedure slow. The current dynamic methods with global excitation are also slow because of the need to either synchronize with the imaging device after equilibrium, or sweep through a range of excitation frequencies. Those methods that excite only a single frequency can only characterize a subset of the dynamic properties, compared to methods that excite a range of frequencies. Moreover, no dynamic elastography method (including the dynamic methods with either local or global excitations) has so far proposed a method of excitation combining multiple frequency components together, so that robust system identification techniques can be employed to identify the tissue properties.

BRIEF SUMMARY OF THE INVENTION

Methods and systems according to some embodiments combine the following:
  Excitation of a region of tissue with a signal containing multiple or a continuum of frequency components
  Measurement of the tissue response to the excitation by rapid or parallel measurements at multiple locations and time instants
  Development of several models of tissue dynamics where the models comprise sets of interconnected linear dynamic systems
  Acquisition of one or more dynamic properties of the tissue by using system identification techniques on the measurements and a particular model
  Use of multiple measurements to accurately and robustly identify the dynamic tissue properties A novel approach for calculating tissue properties considers the measurements as inputs and outputs of a linear dynamic system that models the tissue dynamics. Such a method and system can be constructed from a variety of possible components, including conventional low intensity ultrasound with external vibrators. The result is a unique medical imaging technique that can rapidly and robustly measure new aspects of the dynamics properties of tissue.

An aspect of the invention provides a method and system for imaging the mechanical properties of tissue. The system comprises an exciter to induce dynamic motion of a region of tissue, a device for measuring the resulting displacements and/or velocities at a number of time instances and spatial locations, a computing device for calculating the mechanical properties from the measurements, and a display device to show the calculated properties according to their spatial locations.

The calculation of the mechanical properties is based on a novel approach of creating a specific model of the tissue, and calculating the parameters of the model. By using an excitation containing multiple frequencies and robust system identification techniques, this new imaging approach is extremely effective at calculating the underlying properties of the tissue.

Several embodiments of the exciter and measurement devices are possible. A conventional ultrasound probe may be used for measurement of displacements (from echo data) or velocities (from Doppler data). The output of the ultrasound machine is preferably in the form of radiofrequency echo signals. Alternatively the output can be 1D amplitude modulated signals, 2D images or 3D data sets. The probe may be combined with a vibrator that is pressed onto the surface of the body together with the probe. The vibrators induce the tissue motions and the probe remains stationary to collect the measurements. When pressed against the tissue, the forces generated by the vibrator can induce vibrations in the probe-vibrator assembly itself. To maintain the probe-vibrator assembly stationary, additional vibrators are preferably mounted together with a vibration measurement device. The additional vibrators are controlled to counterbalance the contact forces until the vibration measurement device detects no residual vibrations. Alternatively, the probe and vibrator may be separated and placed on opposite sides of the tissue (such as the breast) while facing each other. Alternatively, the vibrator may be replaced by a needle-based exciter, where the needle is inserted into the tissue and an inner stylet extended outside the cannula and vibrated to induce tissue motion at the needle tip. Alternatively, high intensity focused ultrasound can be produced by an ultrasound transducer, possibly the same transducer used for imaging, to induce tissue motions. In all cases, the excitation produces motion with multiple frequencies or a continuum of frequencies.

Given an excitation of the tissue, and measurements of the resulting motions, one can model the tissue as a set of interconnected linear dynamic systems. In one embodiment, the model is composed of a one-dimensional chain of linear dynamic systems, where the excitation is applied to one end, and motion is induced in all elements through propagation of the forces along the chain. Alternatively, 2D and 3D models of interconnected systems can be used.

The parameters of the model are identified by calculating the best fit to satisfy the equations of motion of the set of elements. Three approaches of this formulation are possible. In the first, the structure of these interconnected systems is decided a priori. In particular, a lumped parametric model is assumed. In the second approach, these interconnected systems components are viewed as linear "black boxes" for which transfer functions are obtained. In the third approach, the transfer functions are assumed to have a parametric structure and their parameter values are estimated in the frequency or time domain.

The first approach uses a lumped parametric model that is derived from finite-element techniques. The finite element model is composed of mass elements connected by springs and dampers. Preferably it is based on realistic models from the field of biomechanics. The method of identifying the parameters of the lumped model is based on fitting the model to the measurements of the motions at each of the elements. The set of identified parameters at each of the measured locations are then used to form an image for display. The effectiveness of this approach is based on the use of multiple measurements from an excitation containing a range of frequencies to produce reliable results in the presence of noise.

The second approach is based on transfer functions, and has the advantage that no a priori modelling assumptions are required other than linearity. Using the same excitation of tissue motion in the previous approach, a transfer function is calculated between tissue motions at adjacent spatial locations by considering one location to be the input and the adjacent location to be the output of a linear dynamic system. Both the magnitude and phase of the transfer function is obtained. Like the first approach, it is the combination of measurements at multiple time instances and an excitation that has significant frequency content that leads to the transfer function method providing reliable tissue properties results in the presence of measurement noise. After obtaining the transfer function, one or more properties of the transfer function can be computed for display.

The third approach is based on a structured transfer function. In this approach, a parametric model is fit to the transfer function in the frequency or time domain. The parameters of the fitted model can be converted into an image for display. With either the first, second or third approach, the result is a meaningful medical image of the dynamic properties of tissue.

BRIEF DESCRIPTION OF THE DRAWINGS

Further aspects and features of the present invention will be evident from the detailed description of the present invention taken in conjunction with the accompanying drawings in which.

DETAILED DESCRIPTION OF THE INVENTION

The following description describes an apparatus and method of imaging the properties of human or animal tissue.

Overview of the Approach

Figure 1:
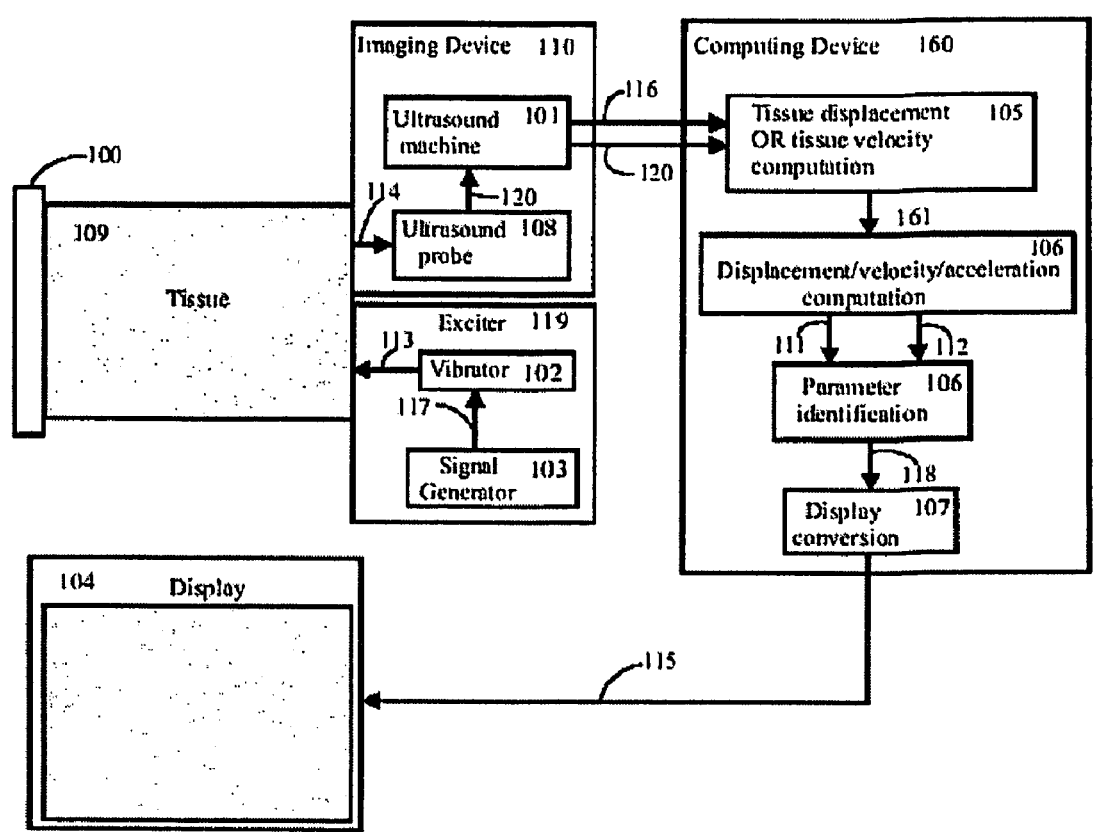
FIG. 1 shows an embodiment of an imaging system using ultrasound measurements and a mechanical external vibrator.

An embodiment of the present invention is shown in FIG. 1. Broadly, the system has an exciter 119 to create mechanical waves in the tissue, an imaging system 110 to capture tissue displacements and/or velocities from the wave motion, a computing device 160 that calculates tissue viscoelastic parameters from the captured tissue displacements and/or velocities, and a display 104 for displaying information based on the resulting set of parameters.

The viscoelastic parameters that are computed by 160 are derived by considering specific models of the tissue being excited. The use of an appropriate model of the tissue, together with the identification of the parameters of this model, makes this new imaging approach extremely effective.

Figure 2:
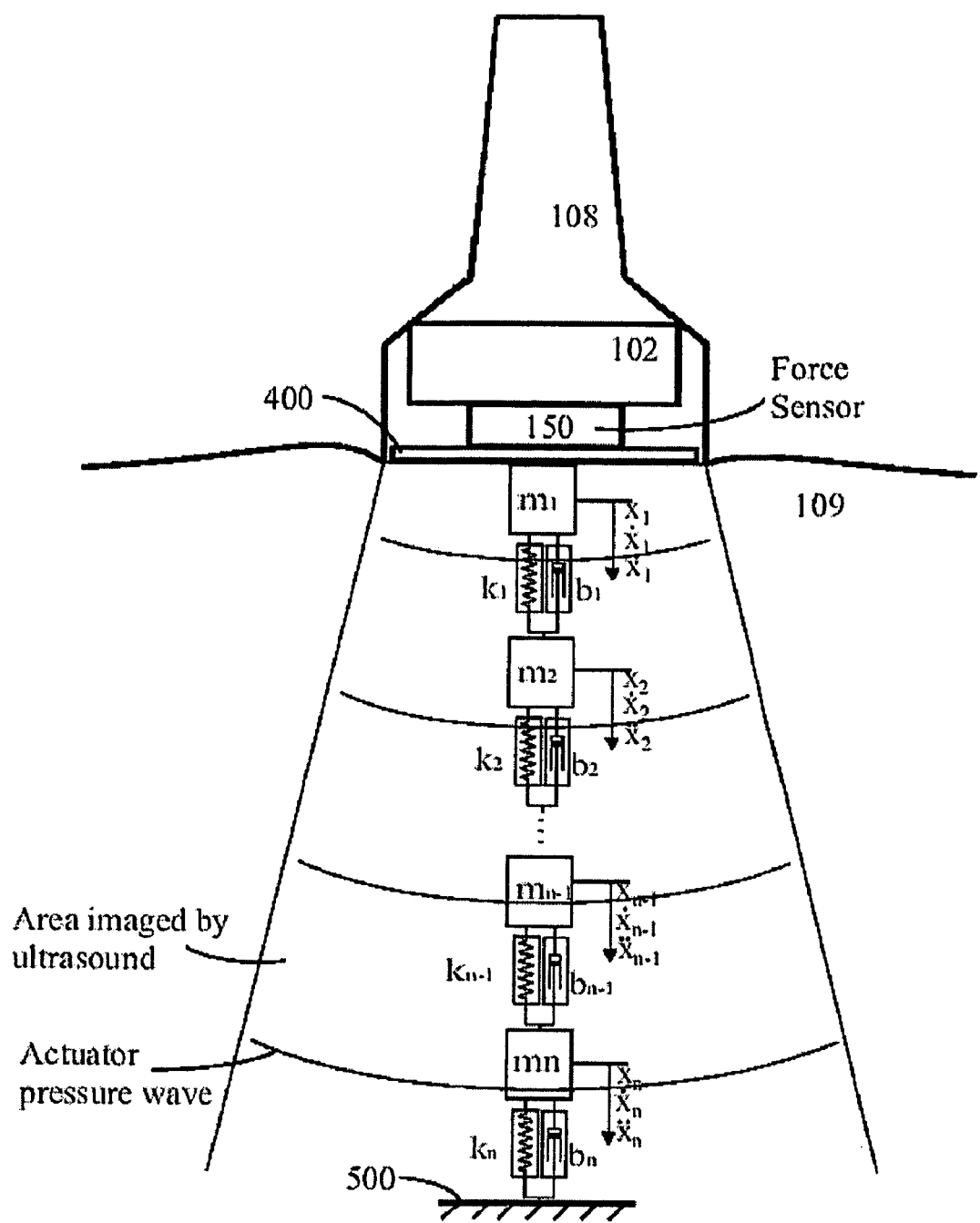
FIG. 2 shows the vibrator and probe assembly with a force sensor together with an embodiment of the tissue model comprising a 1D array of lumped masses interconnected by springs and dampers.
Figure 3:
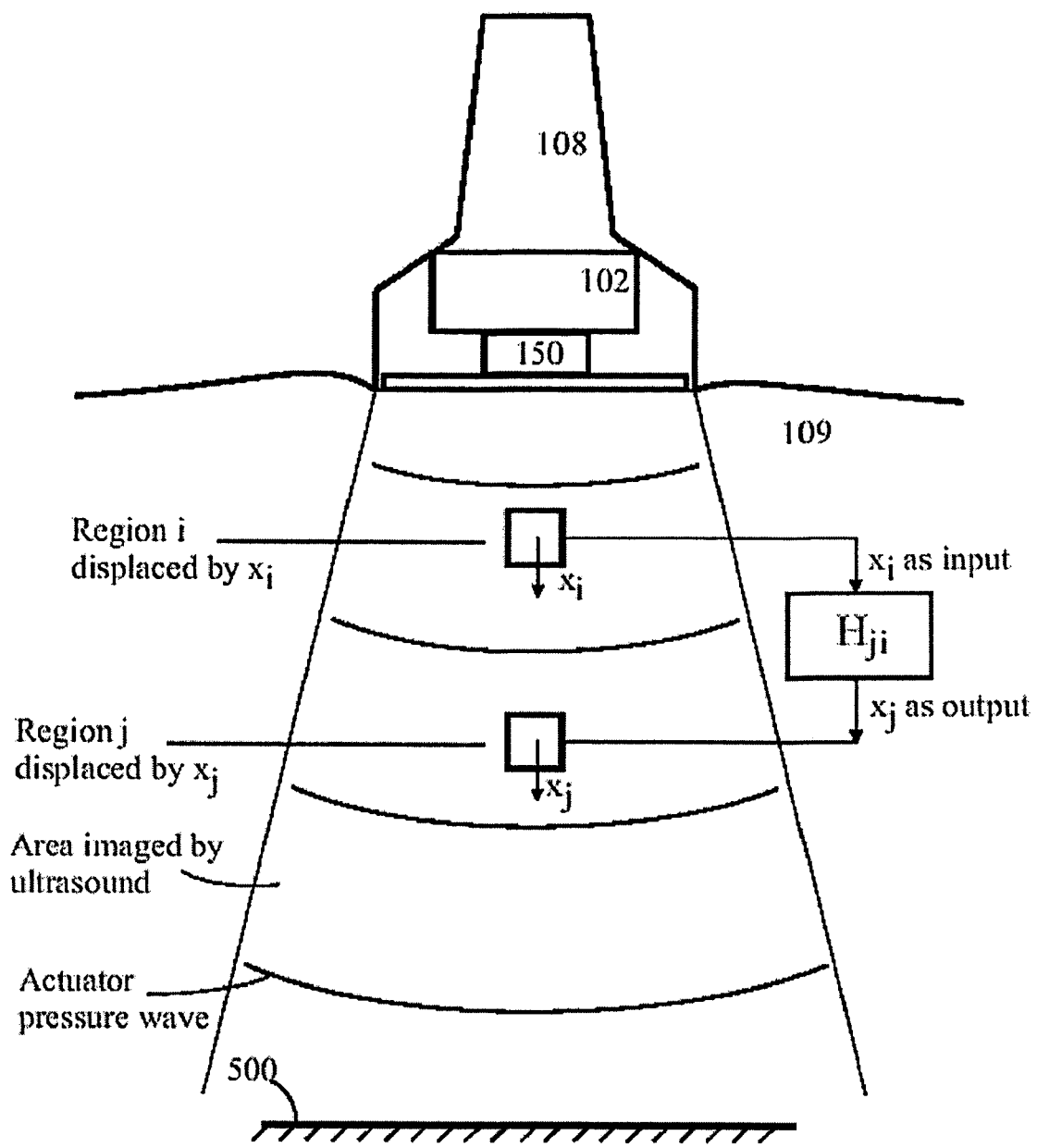
FIG. 3 shows the vibrator and probe assembly with a force sensor. Two regions used in the transfer function approach are indicated.

As shown in FIG. 2 and FIG. 3, the computing block 160 makes use of a tissue model that includes a set of interconnected linear dynamic systems excited by a vibrator coupled to the tissue. The force exerted by the vibrator 102 on the tissue 109 could be measured. The properties of these interconnected dynamic systems are obtained from input and output measurements. The force exerted by the vibrator, and the measured tissue displacements ($x_i$, i=1, ..., n) and/or velocities ($\dot{x}_i$, i=1, ..., n) and/or accelerations ($\ddot{x}_i$, i=1, ..., n) are measured at different locations.

The structure of these interconnected systems could either be decided a priori, giving the tissue an aggregate global model, or, alternatively, these interconnected systems could be left without structure, e.g., as "black boxes" with minimal properties such as linearity.

If the interconnected systems are considered to be structured, the tissue can be considered, for example, to be modelled globally as an interconnected network of masses connected by springs and dampers, as shown in FIG. 2. As will be shown below, the mass, damper and spring values can be obtained by re-writing the equations of motion in a linear-in-parameters form, so the mass, damping and spring parameter values can be obtained by solving a large linear system of equations. The parameter values, or other values derived from the parameter values, can be displayed as intensity, color or other type of maps at their appropriate spatial location in order to obtain a medical image.

If the interconnected systems are considered to be "black boxes", without an a priori structure, then an alternative model is used. For example, as shown in FIG. 3, the motion of a small region of tissue can be considered to be the input $x_i$ of a linear dynamic system whose output $x_j$ is the motion of an adjacent region of tissue. The measurement-based estimation of the motion of the input and output tissue regions in response to an external excitation can then be used to compute a transfer function $H_{ji}$ (either a complex function of frequency, or magnitude and phase functions of frequency) between these two regions. This transfer function will normally characterize the tissue properties between the input and output tissue regions. Dividing the tissue into small regions interconnected by such "black-box" linear dynamic systems, finding the transfer functions associated with these, and displaying some properties of these transfer functions as intensity, color or other types of maps at their appropriate spatial location leads to meaningful medical images characterizing the properties of tissue.

Alternatively, a parametric structure is imposed on the transfer functions described above and the parameters are identified in the frequency domain, after the transfer functions have been computed as complex frequency responses or magnitude and/or phases as described above.

Alternatively, a parametric structure is imposed on the transfer functions and the parameters are identified in time domain, by assuming a auto-regressive-moving-average model whose parameters can be identified by a number of techniques such as recursive least squares, instrumental variables, or maximum likelihood.

Exciter and Imaging Device

In one embodiment of the invention, as shown in FIG. 1, the exciter can include an electromechanical vibrator 102 connected to a signal generator 103. The electrical signals 117 received from the signal generator 103 are converted into motion of the vibrator 102 that, in turn, produces mechanical waves 113 in the tissue. The exciter 119 is capable of a producing a range of force levels and frequencies. It is preferred that the range of forces induces strain levels in the tissue from 0% up to 5%. It is also preferred that the frequencies range from static forces up to 20 Hz or 30 Hz. It is preferred that the exciter 119 produce axial compression waves in the tissue.

It is preferred that the imaging device 110 includes an ultrasound machine 101 and probe 108 capable of imaging the excited tissue at a sufficiently high rate. The motions of the tissue must be measured at a rate greater than twice the highest frequency of excitation. This is so that the motion, according to the Nyquist theorem, can be measured without aliasing. The ultrasound machine produces snapshots of the tissue at multiple instances in time from which the local tissue displacements or velocities can be obtained.

It is preferred that the ultrasound machine 101 produce as output processed digital data 116 that includes at least a subset of the following: a sequence of B-scan images, a sequence of envelope echo signals, a sequence of Doppler data related to tissue velocity. It is preferred that the ultrasound machine 101 also produce as output a sequence of radiofrequency echo signals 120 from the probe 108 that may include some or no digital signal processing.

The processed digital data 116 and the radiofrequency data 120 should be available in real-time after processing at the fastest possible rates. Alternatively, the ultrasound machine 101 may include processing capability that generates directly tissue displacement and/or velocity data 161 in a subset or throughout the entire ultrasound image based on fast on-board signal processing. This eliminates the need for the displacement/velocity computation block 105. It is preferred that the ultrasound machine 101 produces data from scanning a 2D plane within the excited region of interest. Alternatively, the ultrasound machine 101 scans along a 1D line through the excited region of interest. Alternatively, the ultrasound system 101 produces 3D volumetric data by scanning a volume within the excited region of interest. Alternatively, a medical imaging modality other than ultrasound is used, but still satisfies the Nyquist theorem.

Figure 4:
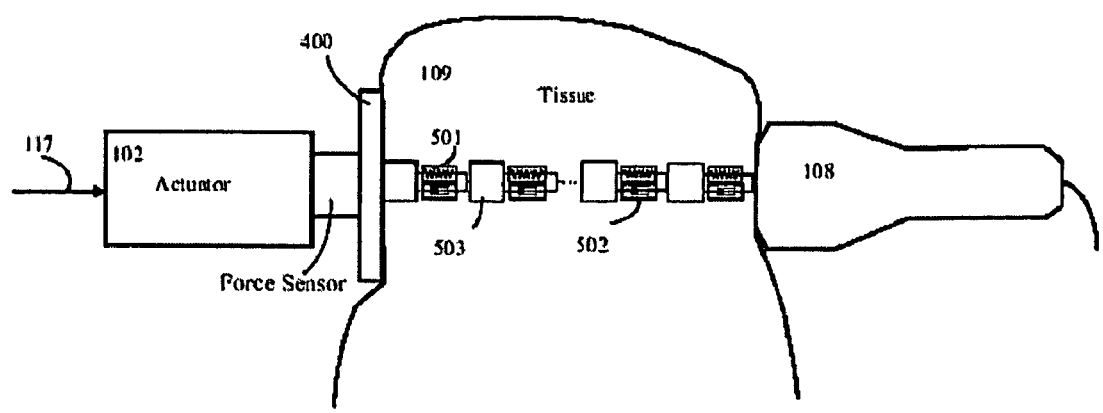
FIG. 4 shows an embodiment of the exciter and measurement device where a vibrator is placed opposite of an ultrasound probe.

In one embodiment of the invention, the vibrator 102 is pressed directly on the skin surface 400 anti-parallel to the ultrasound probe 108 as shown in FIG. 4. Such configuration is possible in breast examinations.

Figure 5:
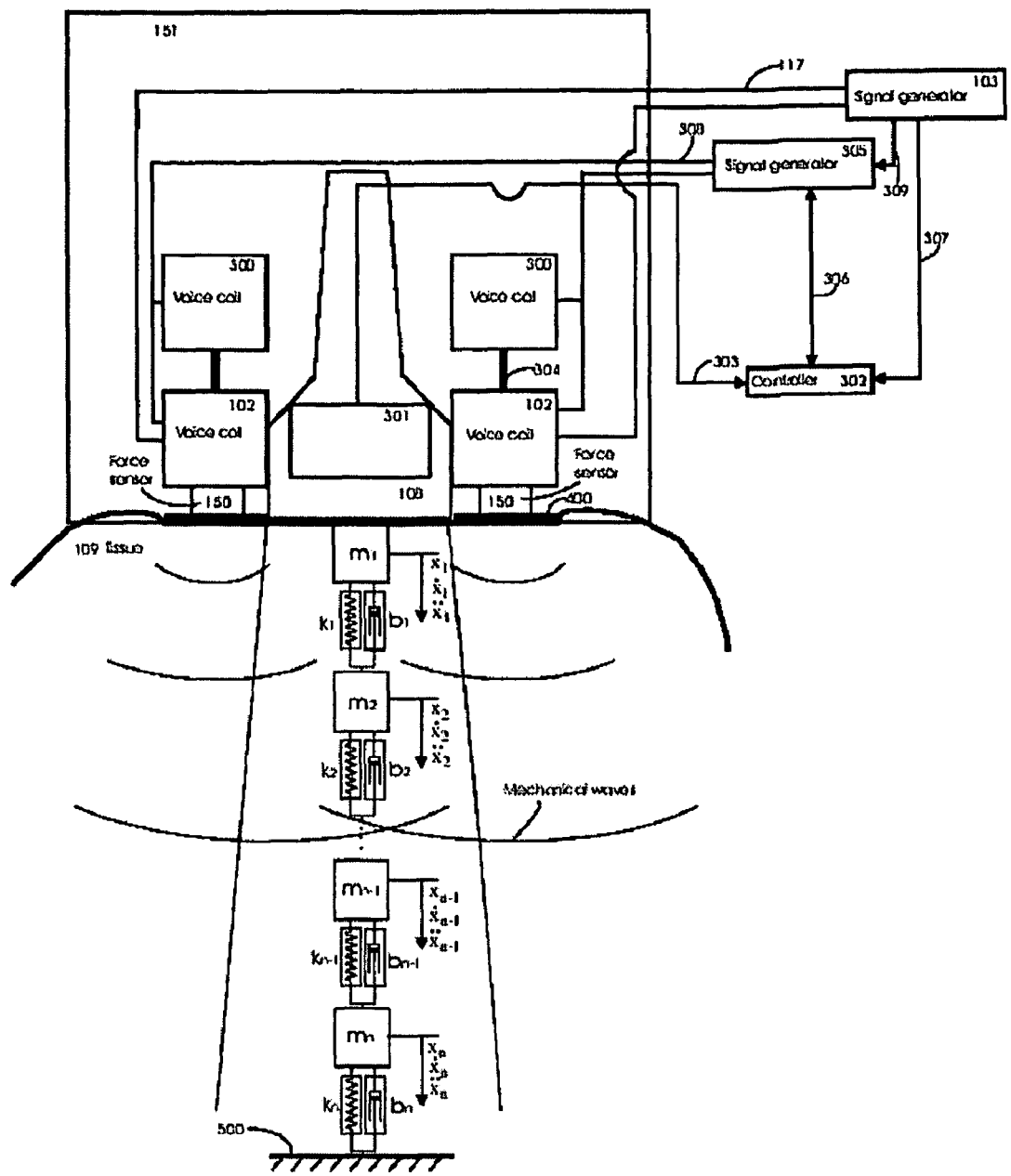
FIG. 5 shows a hand-held vibrator-probe assembly with additional opposing vibrators to cancel residual vibrations.

In another embodiment of the invention, a device combines the tissue exciter and the ultrasound imaging device in the same hand-held unit. An embodiment of this device is shown in FIG. 5. The ultrasound probe 108 is used to acquire tissue images, while one or more vibrators, e.g. voice-coil actuators 102 are used to induce tissue motion according to the signals generated by one or more signal generators 103. A hand-held probe that combines the imaging device and exciter in the same unit may be subject to inertial reaction forces that would cause the entire probe assembly 151 to vibrate in the user's hand. This undesirable effect could be cancelled by using pairs of counteracting vibrators as shown in FIG. 5. Indeed, the vibrators 102 and 300 could be moving in opposite directions in such a way that when the assembly 151 is not in contact with the tissue, the inertial forces on the handle 151 exactly cancel out. Errors in inertial force cancellations may occur because the vibrators 102 are loaded by contact with the tissue while the vibrators 300 are not. Such errors could be eliminated by a controller 302 that uses feedback based on a signal 303 from an accelerometer or other vibration sensor 301 to adjust the command 306 of a signal generator 305 that controls the actuator 300 with the goal of nulling out the vibrations of the assembly 151. There are many algorithms that can be used for such vibration cancellation as known to those skilled in the art of vibration control.

Figure 6:
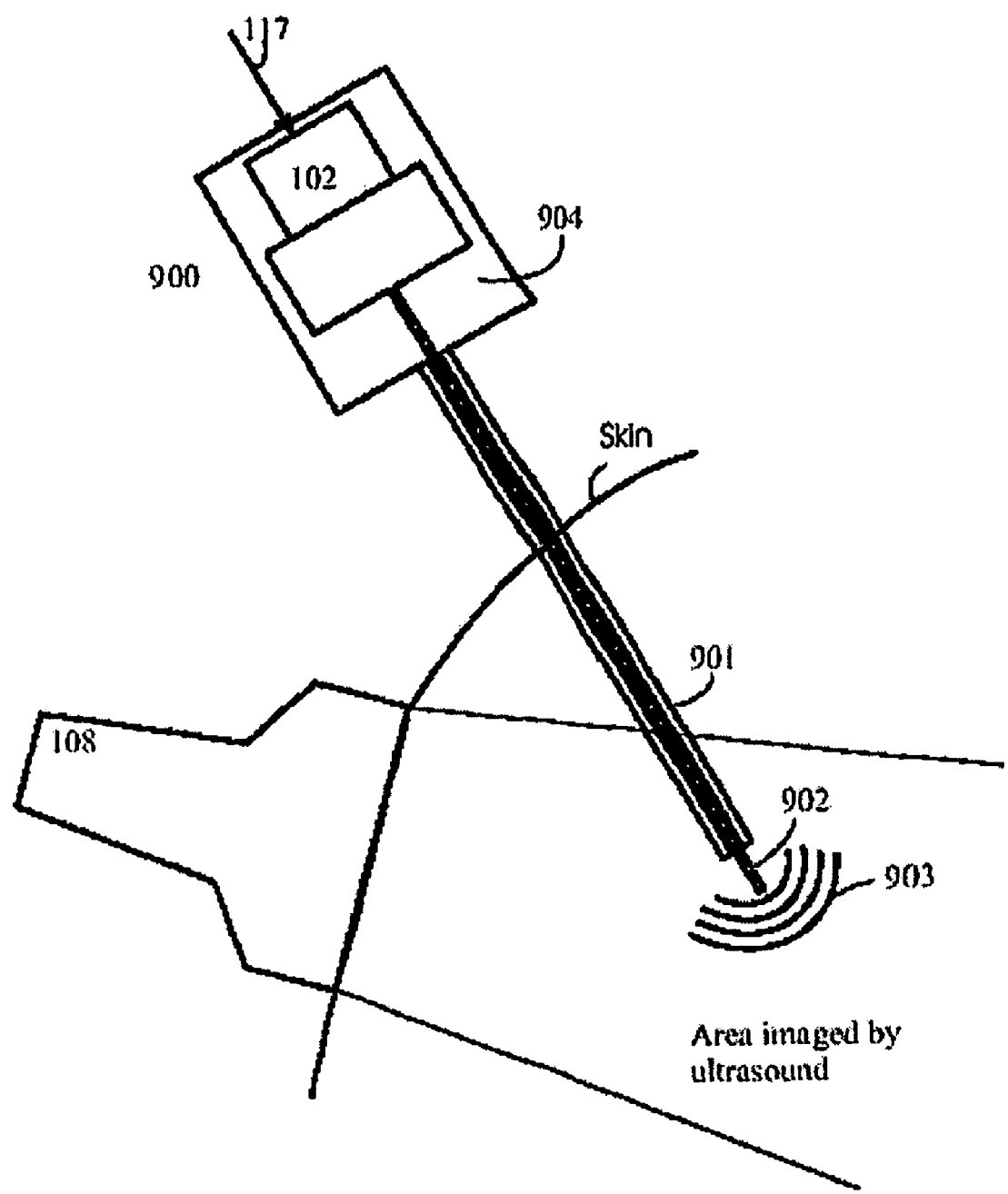
FIG. 6 shows an embodiment of the exciter and measurement device where a needle is inserted in the tissue under an ultrasound probe.

Alternatively, the exciter is a medical needle as shown in FIG. 6. The needle 900 can be inserted so that its tip is in a region of interest, possibly deep within the body. One way in which the needle tip and only the tip can generate mechanical motion is to employ a needle having an outer cannula 901 and an inner stylet 902 that is slightly longer than the cannula. The tissue 903 around the tip of the needle 900 is moved by the stylet 902 which is attached to an vibrator 102 located in a housing 904 and acting between the cannula and the stylet so that the stylet can extend out of the cannula a small distance that is controllable by computer via the signal 117 from a signal generator. The stylet 902 extension motion out of the cannula can have multiple or a continuum of frequency components.

Figure 7:
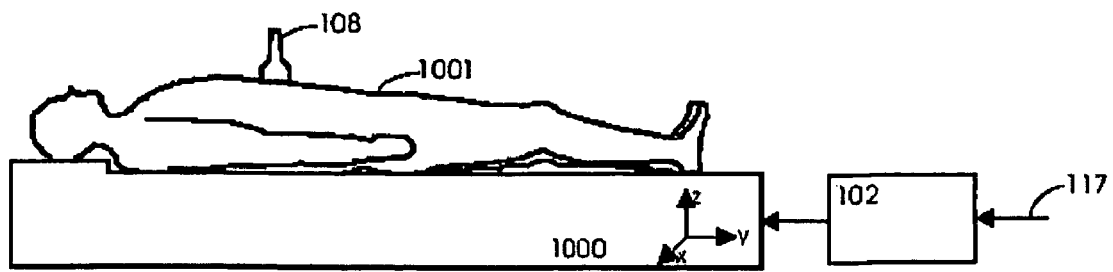
FIG. 7 shows an embodiment of the exciter and measurement device where the support structure holding the subject is connected to a vibrator. The entire subject is therefore excited, including the region imaged by the stationary ultrasound probe.

Alternatively the vibrator 102 is connected to the support structure 1000 holding the patient 1001, as shown in FIG. 7. Motion of the support structure 1000 induces motion in the entire patient 1001, including the region of interest that can be imaged by a fixed ultrasound transducer 108. In this configuration the measurement device 110 is held stationary.

Alternatively, the ultrasound probe 108 can induce forces through high-intensity pulses of focused ultrasound, as described, for example, in Nightingale et al U.S. Pat. No. 6,371,912. The radiation force is produced at several amplitudes and time instances, so that tissue motion occurs at several frequencies. This approach removes the need for an external exciter 119.

Alternatively, the exciter 119 is an ultrasound transducer that applies focused high intensity ultrasound according to the techniques described in Nightingale et al U.S. Pat. No. 6,371,912 and others, while the tissue images are acquired by a separate ultrasound machine 101 and transducer 108. This allows for the excitation and imaging to be performed separately and provides additional flexibility at possibly increased cost.

Displacement or Velocity Measurements

In any of the above embodiments of the exciter 119 and imaging system 110, the resulting measurements of the tissue motions are sent to the computing device 160, as shown in FIG. 1. From these measurements 120 and/or 116, the data is converted by the motion measurement module 105 into measurements of displacement and/or velocity and/or acceleration at each sample in time. Any of the data conversion techniques familiar to practitioners skilled in the art of elastography can be used. Preferably, a technique is used that acquires a set of images, divides each image into small regions, and finds the displacement of each region from one image to the next by maximization of the cross-correlation coefficient. Alternatively, other suitable techniques can be used. Various such techniques for obtaining displacement measurements from ultrasound data are known to those skilled in the art.

Alternatively, the tissue velocity is obtained from the ultrasound machine output 116 in the form of measurements of Doppler shifts. The premise is that the frequency of an echo reflected by a moving target will be shifted compared to the frequency of the incident pulse. This shift is proportional to the tissue velocity. As along as the angle of incidence is known, the shift can be used to calculate velocity. The incidence angle is set by the geometry of the apparatus that produced the direction of excitations and measurements. Most current ultrasound machines can rapidly process the Doppler shifts at a number of different locations, providing velocity measurements in a region of interest. The velocity estimates can be combined with the displacement measurements, or used to calculate the displacement and/or acceleration measurements.

It should be obvious to the skilled in the art that the particular partitioning of image acquisition and processing to generate measurements shown in FIG. 1 can be done in many ways, and depends on the particular structure of the imaging device 110 and the computing device 160.

In particular, the computing device and the medical imaging devices, such as the ultrasound machine, could be the same physical computer. Indeed, there exist personal computer-based ultrasound machines that may have spare computing power so that the tissue displacement/velocity computation block 105 may be included in the ultrasound machine block 101.

Obtaining Tissue Mechanical Properties by Parameter Identification

As described above, the computing block 160 makes use of a tissue model that includes a set of interconnected linear dynamic systems excited by a vibrator coupled to the tissue. Three approaches will be described. In the first, the structure of these interconnected systems is decided globally a priori, with the input to the system being the transducer force or displacement near the transducer. A lumped parametric model is assumed, and in particular a model consisting of interconnected mass-spring-dampers will be considered in detail. In the second, these interconnected systems components are viewed as linear "black boxes" for which transfer functions are obtained. In the third approach, the transfer functions are assumed to have a parametric structure and their parameter values are estimated in the frequency or time domain.

Lumped Parametric Tissue Model For simplicity of exposition, a one-dimensional tissue model is considered, as shown in FIG. 2. The approach can be generalized easily to 2-D and 3-D models. The vibrator 102 as described above and shown in FIG. 2, is used to excite mechanical motions in the tissue at multiple frequencies or over a continuum of frequencies. Filtered white noise is a good choice for the mechanical excitation motion, as such signals have infinitely many or a continuum of frequency components, as described by L. Ljung, "System Identification, Theory For The User", Prentice Hall, 1999, and other parameter identification or control systems texts.

The exciter generates waves in the tissue that cause tissue displacements. The resulting tissue displacements and/or velocities and/or accelerations are measured or are estimated from measurements at a plurality of spatial locations and time instances as described above.

Figure 8:
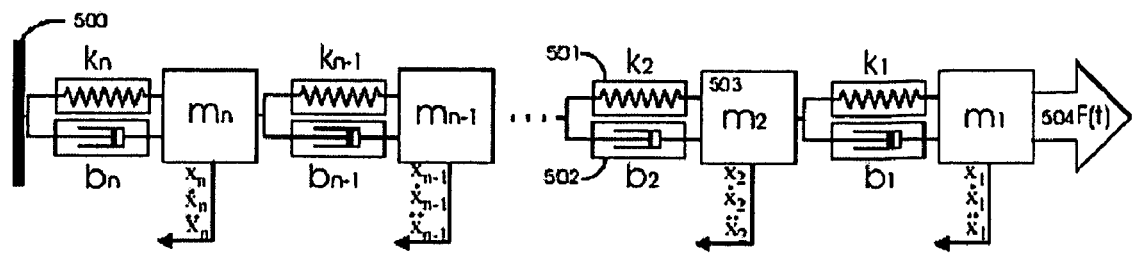
FIG. 8 shows a one-dimensional parametric dynamic model of the tissue.

Tissue properties are calculated by fitting the estimated tissue displacements, velocities and accelerations at a number of time instances to a lumped parametric model of the tissue dynamics, such as the mass-spring-damper system illustrated in FIG. 8. The model relates the excitation (applied force 504 in FIG. 8) to the displacements, velocities and accelerations of the tissue at a number of spatial locations (displacements, velocities and accelerations of the masses in FIGS. 2,4,8,10) that depend on the assumed model (the mass-spring-damper system of FIG. 8). The parameters of the model—which for the mass-spring-damper model of FIG. 8 are the values of all the masses 503, dampers 502 and springs 501—are found by fitting the estimated displacements, velocities and accelerations to the applied force (excitation). This fit can be performed using a least-squares approach. The problem can be formulated as a linear-in-parameters problem.

The lumped parametric model is derived from finite-element techniques (described, for example by K. Bathe in "Finite Element Procedures", Prentice Hall, 1996). The finite element model is composed of mass elements connected by springs and dampers. Preferably it is based on realistic models from the field of biomechanics. The model can be one-dimensional, two-dimensional or three-dimensional. A one-dimensional model is shown in FIG. 8. Each element has an associated mass 503. Between pairs of elements is a spring 501 and a damper 502 arranged in parallel. The spring 501 models the local elasticity of tissue and the damper 502 models the viscosity. The masses model the local density. Both springs 501 and dampers 502 are linear. Other models are possible by using different configurations of springs 501 and dampers 502 between the elements. Because the model must include mass elements 503 and at least one spring 501 or damper 502 connecting the elements, there are a minimum of two types of parameters to be identified. The model may consist of mass elements connected to each neighbor by one spring 501 and one damper 502 arranged in parallel.

The method of identifying the parameters of the lumped model is based on applying a force with a significant frequency content (i.e. containing many spectral lines, or has a Fourier transform that is non-zero over a continuum of frequencies), and fitting the model to the measurements of the resulting motions at each of the elements. No particular provision needs to be made for boundary conditions, as these boundary conditions determine the values of the mass-springdamper parameters. For example, if the mass $m_n$ in FIG. 8 is connected to a bony structure or it is constrained by a very stiff boundary, the spring and/or damper parameters $k_n$, $b_n$ will have high values. If, on the other hand, the tissue region modeled around $m_n$ is soft, the associated spring and damper values will be small. In the one-dimensional model shown in FIG. 8, the excitation 504 is applied to one end of the chain, and the other end 500 is held stationary to a fixed boundary. Under these boundary conditions, the equations of motion for all n elements at time t can be expressed as $$\underbrace{\begin{bmatrix} m_1 & 0 & 0 & \cdots & 0 \\ 0 & m_2 & 0 & \cdots & 0 \\ 0 & 0 & m_3 & \cdots & 0 \\ \vdots & & & \ddots & 0 \\ 0 & 0 & 0 & \cdots & m_n \end{bmatrix}}_{M} \underbrace{\begin{bmatrix} \ddot{x}_1 \\ \ddot{x}_2 \\ \ddot{x}_3 \\ \vdots \\ \ddot{x}_n \end{bmatrix}(t)}_{a(t)}$$

$$\underbrace{\begin{bmatrix} b_1 & -b_1 & 0 & 0 & \cdots & 0 \\ -b_1 & (b_1+b_2) & -b_2 & 0 & \cdots & 0 \\ 0 & -b_2 & (b_2+b_3) & -b_3 & \cdots & 0 \\ \vdots & & & & \ddots & 0 \\ 0 & 0 & 0 & \cdots & b_{n-1} & b_n+b_{u-1} \end{bmatrix}}_{H} \underbrace{\begin{bmatrix} \dot{x}_1 \\ \dot{x}_2 \\ \dot{x}_3 \\ \vdots \\ \dot{x}_u \end{bmatrix}(t)}_{u(t)}$$

$$\underbrace{\begin{bmatrix} k_1 & -k_1 & 0 & 0 & \cdots & 0 \\ -k_1 & (k_1+k_2) & -k_2 & 0 & \cdots & 0 \\ 0 & -k_2 & (k_2+k_3) & -k_3 & \cdots & 0 \\ \vdots & & & & \ddots & 0 \\ 0 & 0 & 0 & \cdots & -k_{n-1} & k_n+k_{n-1} \end{bmatrix}}_{K} \quad (2)$$

$$\begin{bmatrix} x_1 \\ x_2 \\ x_3 \\ \vdots \\ x_n \end{bmatrix}(t) = \begin{bmatrix} f \\ 0 \\ 0 \\ \vdots \\ 0 \end{bmatrix}(t) = u(t)$$

$$Ma(t) + Bv(t) + Kx(t) = a$$

where $m_i$ is the mass parameter of element i, $b_i$ is the viscosity parameter between $m_i$ and $m_{i+1}$, $k_i$ is the elasticity parameter between $m_i$ and $m_{i+1}$, $x_i(t)$ is the displacement measurement of the $i^{th}$ element in the model at time t, $v_i(t) = \dot{x}_i(t)$ is the velocity measurement ($dx_i/dt$) at time t, $a_i(t) = \ddot{x}_i(t)$ is the acceleration measurement ($d^2x_i/dt^2$) at time t, and $f(t)$ is the force measurement at time t. The definitions of the matrices M, B, K and $x(t)$, $\dot{x}(t)$ and $\ddot{x}(t)$ are clear from (1).

The above set of equations can be combined and rearranged in a form that is linear in model parameters as follows:

$$\varphi^T(t)\theta = u(t) \quad (3)$$

where u contains the excitation forces and is defined in (1), $\varphi$ contains the measurements of motion of each element (tissue region) as a response to the applied excitation, $$\varphi^T(t) = \begin{bmatrix} a_1 & 0 & \cdots & 0 & v_1-v_2 & 0 & \cdots & 0 & 0 & x_1-x_2 & 0 & 0 & \cdots & 0 & 0 \\ 0 & a_2 & \cdots & 0 & v_2-v_1 & v_2-v_3 & \cdots & 0 & 0 & x_2-x_1 & x_2-x_3 & 0 & \cdots & 0 & 0 \\ \vdots & & \ddots & \vdots & \vdots & & & & & \vdots & & & \cdots & & \vdots \\ 0 & 0 & \cdots & a_n & 0 & 0 & \cdots & v_n-v_{n-1} & v_n & 0 & 0 & 0 & \cdots & x_n-x_{n-1} & x_n \end{bmatrix} \quad (4)$$

and $\theta$ is a vector of entries of M, B and K, as follows:

$$\theta = \begin{bmatrix} m_1 \\ m_2 \\ \vdots \\ m_n \\ b_1 \\ b_2 \\ \vdots \\ b_n \\ k_1 \\ k_2 \\ \vdots \\ k_n \end{bmatrix} \quad \text{and} \quad u(t) = \begin{bmatrix} f(t) \\ 0 \\ 0 \\ \vdots \\ 0 \end{bmatrix} \quad (5)$$

There are 3n unknowns ($m_i$, $b_i$, and $k_i$, i=1, ..., n) in $\theta$ and n equations in (3). This is insufficient to determine the parameters in $\theta$. By measuring the displacement, velocity and acceleration at m different time instants $t_i$, i=1, ..., m, the problem can be constrained. The number of time instances m required to determine the parameter $\theta$ in (3) depends on how accurately a tissue model of order n can determine the tissue behavior in response to the excitation f(t), and on the frequency content of f(t). This is why it is best for the spectrum of f(t) to have many spectral lines or to be supported by a continuum of frequencies.

The next step is to identify the parameters $m_i$, $b_i$, and $k_i$ from these equations by using the measurements $x_i(t)$, $\dot{x}_i(t)$ and $\ddot{x}_i(t)$. The measurements are made at multiple time instants so that this equation of motion can be expressed multiple times.

Then by using ordinary least squares (see for example L. Ljung, "System Identification, Theory For The User", Prentice Hall, 1999) the parameters can be found. The system of equations (3) can be written for several measurements, and can be stacked together to produce a set of over-constrained equations as shown below:

$$\underbrace{\begin{bmatrix} \varphi^T(t_1) \\ \varphi^T(t_2) \\ \vdots \\ \varphi^T(t_m) \end{bmatrix}}_{\Phi} \theta = \underbrace{\begin{bmatrix} u(t_1) \\ u(t_2) \\ \vdots \\ u(t_m) \end{bmatrix}}_{u} \quad (6)$$

Note that it is the typical situation that the number of equations $m_n$ in (6) is much greater than n and there are many redundant equations, with the system being significantly overconstrained.

The solution that minimizes the Euclidean error $\|\Phi\theta-u\|_2$ in (6) is given by $$\theta=(\Phi^T\Phi)^{-1}\Phi^T u \qquad (7)$$

as long as $(\Phi^T\Phi)$ is invertible. The conditions for $(\Phi^T\Phi)$ to be invertible have been studied in a number of papers and are summarized by L. Ljung, "System Identification, Theory For The User", Prentice Hall, 1999. $(\Phi^T\Phi)$ will be invertible as long as the sequence $\phi(t)$ is persistently exciting and sufficient measurements m are collected. This will normally be the case if the excitation f(t) contains many sinusoids (at least as many as half the number of parameters n, but preferable many more) or the spectrum of f(t) is supported on a frequency interval (true if f(t) is low-pass filtered white noise, for example).

Any suitable approach may be used to find $\theta$. Many approaches for finding $\theta$ in (6) have been developed in the field of parameter identification. These can be implemented by one skilled in the art of system parameter identification.

For example, an alternative to (7) is the use of recursive least squares. As an alternative to ordinary least squares, the use of instrumental variables can improve the solution when noise is present on the measurements.

Furthermore, it will be obvious to one skilled in the art that the above approach which was detailed above for specific matrices M, B and K in (1) can be extended to models derived from the Finite Element Method for which M, B and K have different forms. For example, if the mass-spring model for the tissue is extended to have spring connections not only between adjacent masses, the matrix K will change form, and so will the matrices $\phi(t)$ and $\theta$ in (3). Nevertheless, linearity in parameters is still preserved, and the approach outlined above works in exactly the same overall manner.

Parameter Identification from a Subset of Measurements

It is often the case that only tissue displacements are measured. However, velocities and accelerations are derived from the displacement measurements so that the same linear equation form as (3) results with similar method of solution.

Indeed consider (2). In the Laplace domain, this equation becomes $$Ms^2 X(s)+BsX(s)+KX(s)=U(s) \qquad (8)$$

where X and U are the Laplace transforms of x and u.

Applying the filter $$\frac{1}{(s+a)^2}$$

to both left and right sides of equation (8) leads to:

$$M\frac{s^2}{(s+a)^2}X(s)+B\frac{s}{(s+a)^2}X(s)+K\frac{1}{(s+a)^2}X(s)=\frac{1}{(s+a)^2}U(s) \qquad (9)$$

In the above, one skilled in the art recognizes that $$\frac{s^2}{(s+a)^2}X(s)$$

approximates the Laplace transform of the vector of accelerations $\ddot{x}(t)$, $$\frac{s}{(s+a)^2}X(s)$$

approximates the Laplace transform of the vector of velocities $\dot{x}$, with the filters $$\frac{s}{(s+a)^2} \quad \text{and} \quad \frac{s^2}{(s+a)^2}$$

approximating a derivative and double derivative operation.

The positive parameter a has the interpretation of cutoff frequency of the above differentiator filters, and is normally selected in practice to be at least ten times larger than the frequency with which the tissue displacements are sampled by the tissue imaging system.

If we now change the definitions of a, v, x and u from (2) and we let a(t) be the inverse Laplace transform of $$\frac{s^2}{(s+a)^2}X(s),$$

v(t) be the inverse Laplace transform of $$\frac{s}{(s+a)^2}X(s),$$

x(t) be the inverse Laplace transform of $$\frac{1}{(s+a)^2}X(s),$$

and u(t) be the inverse Laplace transform of $$\frac{1}{(s+a)^2}U(s),$$

we obtain again the equation (2)

$$Ma(t)+Bv(t)+Kx(t)=u \qquad (10)$$

which can be put in the same form as (3).

Clearly the vector sequences u(t), x(t), v(t) and a(t) can be obtained from filtering tissue displacement and applied force data, and with the same definition for $\theta$ as in (3), the solution method and the comments related to the various approaches to obtaining an estimate for $\theta$ are exactly the same as discussed before. The difference is that $\phi^T(t)$ and u(t) have slightly different definitions here than in equation (3) because now they are based on estimates of velocity and acceleration obtained for displacement measurements, and are not direct measurements of velocity and acceleration.

Figure 9:
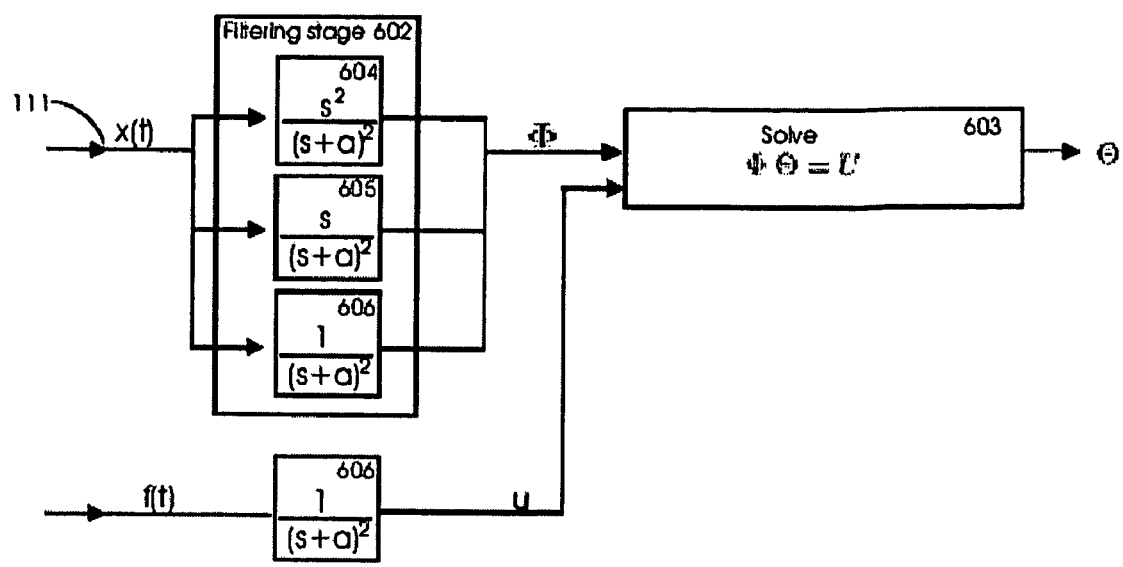
FIG. 9 shows the parameter identification method using only displacement data.
Figure 10:
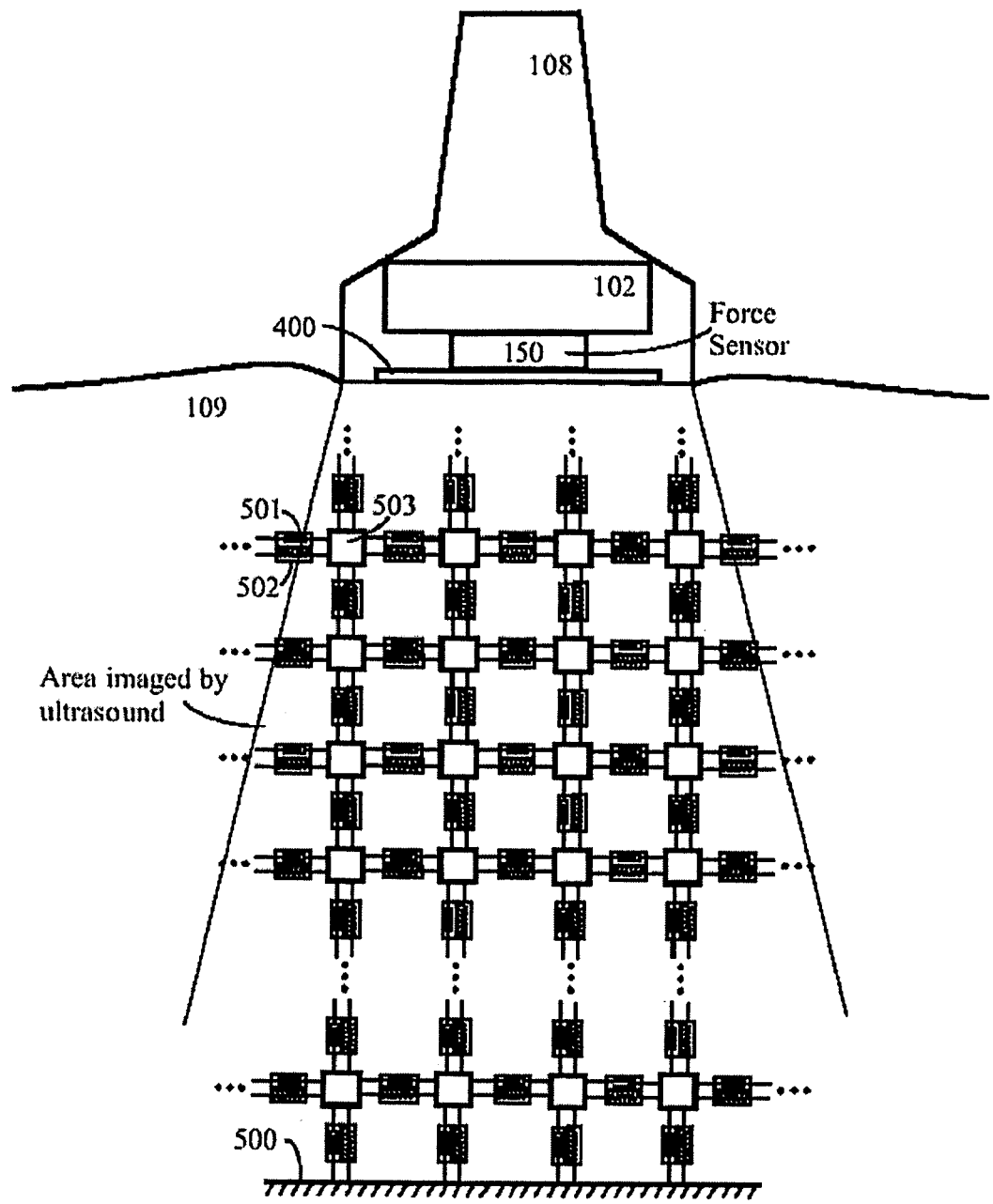
FIG. 10 shows the vibrator and probe assembly with a force sensor together with an embodiment of the tissue model comprising a 2D array of lumped masses interconnected by springs and dampers.

An overview of this filtering method that can be used to fit mass, damping and stiffness parameters from displacement measurements only is shown in FIG. 9. The measurements $x_i(t)$ are stacked together into a single vector x(t) 111 as shown in (1). The first step 602 consists of filtering the measured displacements 111 and filtering (606) the measured force. The block 602 and 606 also assemble the data into matrices $\Phi$ and u as required by (6). The second stage 603 solves the equations for the parameters in $\theta$. It is possible that only tissue velocities are measured, and the displacements and accelerations are derived from the velocity measurements. This could be the case when the tissue velocity is measured with Doppler ultrasound, for example. Again the same form of solution can be found from the equations of motion, but different filters are used.

Indeed, consider again equation (2), written in the Laplace domain with V(s) denoting the Laplace transform of v(t):

$$MsV(s) + BV(s) + K\frac{1}{s}V(s) = U(s) \quad (11)$$

Applying a first order filter $$\frac{1}{(s+a)}$$

to both sides of the equation leads to $$M\frac{s}{s+a}V(s) + B\frac{1}{s+a}V(s) + K\frac{1}{s(s+a)}V(s) = \frac{1}{s+a}U(s) \quad (12)$$

If we let v(t) be the inverse Laplace transform of $$\frac{1}{(s+a)}V(s),$$

a(t) to be the inverse Laplace transform of $$\frac{s}{(s+a)}V(s),$$

x(t) to be the inverse Laplace transform of $$\frac{1}{s(s+a)}V(s),$$

and u(t) to be the inverse Laplace transform of $$\frac{1}{(s+a)}U(s)$$

we obtain again the equation $$Ma(t)+Bv(t)+Kx(t)=u \quad (13)$$

which can be put in the same form as (3), as before. The filter $$\frac{1}{s(s+a)}$$

applied to velocity is not stable because of its integrator component and may lead to very large values of the position estimate. One can replace the filter with an approximation $$\frac{1}{(s+\varepsilon)(s+a)}$$

where $\epsilon$ is a small positive number.

It is obvious that if the tissue displacement and velocities are measured, such as can be done for example, by considering ultrasound radio-frequency data and ultrasound Doppler measurements from 116 of FIG. 1 at the same time, that these can be used in the tissue model equation (2), with the tissue acceleration being derived from either the position or velocity measurements. The same procedure as outlined above can be followed.

Parameter Identification Without Force Measurements

There may be instances in which the measurement of the force applied by the exciter to the tissue is not feasible because of cost or difficulty of assembly. Nevertheless, the parameters can still be identified in the proposed mass-spring-damper tissue model by replacing the force applied to the tissue with tissue displacement measurements.

Indeed, the equation of motion of the system of masses shown in FIGS. 2, 8, starting from mass $m_2$, has the same form as (1), except that force on the right hand side becomes now dependent on the displacements and velocities between $m_1$ and $m_2$:

$$\underbrace{\begin{bmatrix} m_2 & 0 & \cdots & 0 \\ 0 & m_3 & \cdots & 0 \\ \vdots & & \ddots & 0 \\ 0 & 0 & \cdots & m_n \end{bmatrix}}_{M'} \underbrace{\begin{bmatrix} \ddot{x}_2 \\ \ddot{x}_3 \\ \vdots \\ \ddot{x}_n \end{bmatrix}}_{a(t)}(t) \quad (14)$$

-continued $$\overbrace{\begin{bmatrix} b_2 & -b_2 & 0 & 0 & \cdots & 0 \\ -b_2 & (b_2+b_3) & -b_3 & 0 & \cdots & 0 \\ 0 & -b_3 & (b_3+b_4) & -b_4 & \cdots & 0 \\ \vdots & & & \ddots & & 0 \\ 0 & 0 & 0 & \cdots & b_{n-1} & b_n+b_{n-1} \end{bmatrix}}^{B'} \overbrace{\begin{bmatrix} \dot{x}_2 \\ \dot{x}_3 \\ \vdots \\ \dot{x}_n \end{bmatrix}}^{\dot{e}(t)}(t)$$

$$\overbrace{\begin{bmatrix} k_2 & -k_2 & 0 & 0 & \cdots & 0 \\ -k_2 & (k_2+k_3) & -k_3 & 0 & \cdots & 0 \\ 0 & -k_3 & (k_3+k_4) & -k_4 & \cdots & 0 \\ \vdots & & & \ddots & & 0 \\ 0 & 0 & 0 & \cdots & -k_{n-1} & k_n+k_{n-1} \end{bmatrix}}^{B'} \overbrace{\begin{bmatrix} x_2 \\ x_3 \\ \vdots \\ x_n \end{bmatrix}}^{x(t)}(t) = \begin{bmatrix} f \\ 0 \\ 0 \\ \vdots \\ 0 \end{bmatrix}(t) = u(t)$$

where now f(t) is defined by $$f = k_1(x_1(t) - x_2(t)) + b_1(\dot{x}_1(t) - \dot{x}_2(t)) \quad (15)$$

This becomes $$M'a(t) + B'v(t) + K'x(t) + b_1(\dot{x}_2(t) - \dot{x}_1(t)) = k_1(x_1(t) - (t)) \quad (16)$$

which can be written in the linear form $$\varphi'^T(t)\theta' = k_1(x_2(t) - x_1(t)) \quad (17)$$

where slightly changed definitions $\varphi'$ and $\theta'$ of $\varphi$ and $\theta$ are employed:

$$\theta' = \begin{bmatrix} m_2 \\ \vdots \\ m_n \\ b_2 \\ \vdots \\ b_n \\ k_2 \\ \vdots \\ k_n \\ b_1 \end{bmatrix} \text{ and} \quad (18)$$

$$\varphi'^T(t) = \begin{bmatrix} a_2 & \cdots & 0 & v_2-v_3 & \cdots & 0 & 0 & x_2-x_3 & 0 & \cdots & 0 & 0 & \dot{x}_2(t)-\dot{x}_1(t) \\ & \ddots & \vdots & & & \vdots & & & \cdots & & \vdots & & 0 \\ 0 & \cdots & a_n & 0 & \cdots & v_n-v_{n-1} & v_n & 0 & 0 & \cdots & x_n-x_{n-1} & x_n & 0 \end{bmatrix} \quad (19)$$

Since $x_1(t)$ and $x_2(t)$ are measured by the imaging system, this equation can be used to solve for the tissue parameters relative to the value of $k_1$, by the techniques described above.

The number of unknowns in $\theta$ is decreased by two because $m_1$ and $k_1$ no longer need to be identified. The $b_1$ term is retained as the last entry in $\theta$. The matrix of measurements $\varphi'$ becomes $(n-1) \times (3(n-1)+1)$ whereas the $\varphi$ term of equation (3) is $n \times 3n$. Here the mass $m_1$ and $k_1$ terms are not identified. The solution therefore only provides elasticity, damping and mass values relative to $k_1$, but these can still be displayed. Similarly, the removal of the force term can also be applied to the variations of the parameter identification method where only a subset of the measurements are available.

To the skilled in the art, it should be obvious from the above derivation that the displacement at any region of tissue, say corresponding to a mass $m_j$ in the network of mass-spring-dampers illustrated in FIGS. 2,4,8 can be used to derive a tissue force on the adjacent mass $m_{j+1}$ and the parameters $m_i$, $k_i$, $b_i$ for $i=j+1, j+2, \ldots, n$ of the mass-spring system can be identified by the technique outlined above relative to the value of $k_j$.

Other parameter identification techniques, such as regularization approaches could also be employed to include, for example, a priori knowledge such as constraints on the parameters. In particular, one expects that a mass-spring-model for the tissue will generate positive values for the values of the mass, spring and damper parameters. In order to improve the results of minimizing the error of (6) in the presence of noise, constraints such as $m_i \geq 0$, $b_i \geq 0$, $k_i \geq 0$, $i=1, \ldots, n$ may be added and a solution to a constrained problem can be computed. Fast algorithms for such computations have been presented, for example, in the field of medical image reconstruction. As well, in the above tissue model, the mass component can be neglected by either setting the mass parameters to zero (this leads to a linearized model (3) that has only 2n not 3n parameters), or by considering that the tissue density is constant, in which case there is only one mass parameter to be identified. Thus prior knowledge can be embedded easily in the proposed approach for tissue parameter identification. In any of the above embodiments of the parameter identification method, the values of the parameters can be constrained using a priori information about the tissue properties. In one embodiment, the range of possible values for one or more parameters may be restricted to a realistic range. In another embodiment, the values for one or more parameters may be set to their expected values, and the variable removed from the list of unknown parameters in θ. The smaller number of unknowns in the equations of motion make it easier to perform the fit to the measurements.

Although this approach has been derived for a one-dimensional model, similar derivations are possible for two-dimensional (see FIG. 10) and three-dimensional models.

Calculation of the Mechanical Properties from Transfer Functions

Some embodiments of the invention use an alternative method for calculating the mechanical properties of tissue. This alternative method is based on transfer functions, and has the advantage that no a priori modelling assumptions are required other than linearity, and that the inputs used to derive tissue parameters are collocated with the regions of tissue analyzed.

As in the previous methods, an exciter 119 produces mechanical motions in a target tissue at multiple frequencies. The tissue displacement or velocities are measured at a plurality of spatial locations at a number of time instances by a medical imaging system as described above. The two adjacent regions where displacement or velocites are measured in the tissue are illustrated in FIG. 3 and have displacements $x_i(t)$ and $x_j(t)$. While it is preferred that these regions be adjacent along the axis of tissue motion, as illustrated in FIG. 3, transfer functions between regions adjacent along the axis orthogonal to tissue motion would also give tissue property information, and are related to shear effects.

Figure 11:
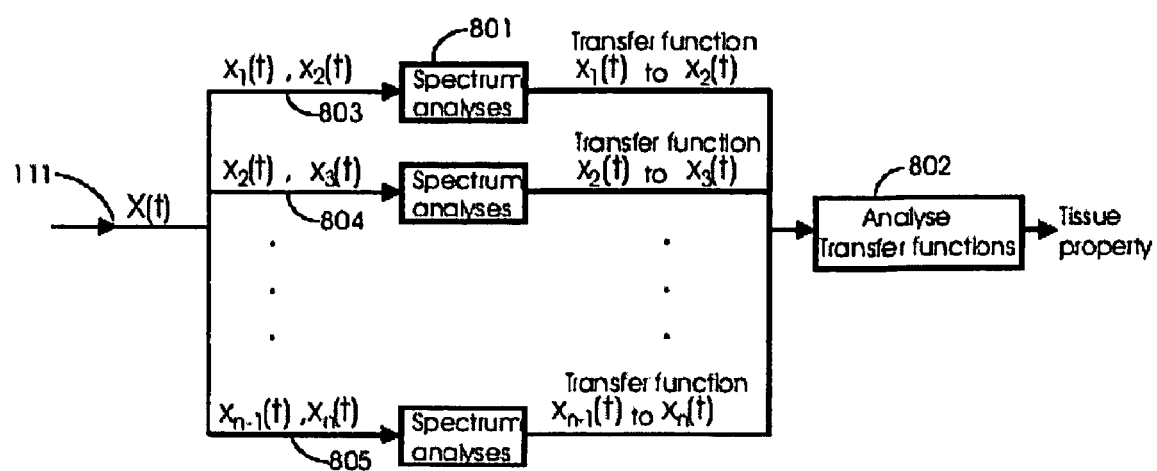
FIG. 11 shows the steps for the transfer function calculations using spectrum analysis.

As shown in FIG. 11, the transfer functions between tissue motions at adjacent spatial locations are calculated by a spectral analysis block 801 by considering one location with displacement $x_i$ to be the input and an adjacent location with displacement $x_j$ to be the output of a linear dynamic system. Both the magnitude and phase of the transfer function are obtained. In FIG. 3, $x_i(t)$ is an input sequence of tissue displacements and $x_j(t)$ is and output sequence of tissue displacements. The transfer function between element i and element j is calculated according to known principles, see for example L. Ljung, "System Identification, Theory For The User", Prentice Hall, 1999. First, the power spectral density $P_{x\_i\ x\_i}(\omega)$ of element $x_i(t)$ is computed. Then the cross spectral density $P_{x\_i\ x\_j}(\omega)$ between elements i and j is computed. Then the complex transfer function is computed as follows:

$$H_{ji}(\omega) = P_{x_i x_i}(\omega) / P_{x_i x_j}(\omega) \quad (20)$$

The quality of the transfer function depends on the quality of the measurements, and the type of tissue excitation. The transfer function is a function of frequency. For the transfer function to be meaningful at a given frequency, it is required that the excitation be sufficiently large at that frequency. As discussed above within the context of the parametric tissue model, the excitation should contain many spectral lines (sinusoids) or have a frequency spectrum that is supported on the frequency range of interest for tissue characterization. Typically, the tissue properties of interest lie from very low frequency (reported relaxation time of tissue can be seconds, meaning that the frequency response may prove useful down to a fraction of a Hertz), to a useful upper frequency limit that is determined by the speed of the imaging system, as discussed before, and which could be of the order of 20-30 Hz.

The reliability of the transfer function can be checked by computing the coherence function corresponding to each calculated transfer function. The coherence function between $x_i$ and $x_j$ is given by $$C_{x_i x_j}(\omega) = |P_{x_i x_j}(\omega)|^2 / (P_{x_i x_i}(\omega) P_{x_j x_j}(\omega)) \quad (21)$$

where $|P_{x\_i\ x\_j}(\omega)|$ is the magnitude of the cross spectral density between $x_i$ and $x_j$, and $P_{x\_i\ x\_i}(\omega)$ and $P_{x\_j\ x\_j}(\omega)$) are the power spectral densities of $x_i$ and $x_j$. The coherence function gives information about the linearity of the data on the frequency range the system is excited. Its value is always between 0 and 1. A high coherence function indicates that most of the energy in the input signal at a given frequency appears at the output at the same frequency, and therefore a high coherence function indicates good confidence that the system is linear and the signal to noise ratio is good. Therefore the coherence function can be used as a check to ensure confidence in the results.

It is the combination of measurements at multiple time instances and resulting from an excitation that has significant frequency content that leads to the transfer function method providing reliable tissue properties results in the presence of measurement noise.

As shown in FIG. 11, after obtaining the transfer function, one or more properties of the transfer function can be computed for display by a transfer function analysis block 802.

In one embodiment, the displayed property of the transfer function is its low-frequency magnitude. The magnitude of the transfer function at a frequency of zero is expected to be related simply only to elasticity and not density or viscosity. An explanation for this can be found by observing equation (1) where the velocity and acceleration values are set to zero. Only the elasticity terms remain.

In another embodiment, the displayed property is an average of the magnitude of the transfer function at low frequencies where it is approximately constant. The reason to perform an average is to reduce the influence of measurement error on the estimation of the tissue elasticity. But averaging over a frequency range where the transfer function magnitude is no longer linear would introduce additional errors and should be avoided. The linearity of the transfer function at low frequencies is checked by using the corresponding coherence functions.

The above approach is summarised in FIG. 11. Following mechanical excitation of the tissue, displacement data 111 in a number of adjacent tissue regions is collected as pairs of tissue displacements 803. Spectrum analysis 801 blocks using the approach described above and summarized in (20) are used to compute transfer function 804. Properties of the transfer function, such as low frequency gain, low-frequency average, etc. are computed by an analysis block 802, which generates tissue properties data that can be displayed at a location collocated with the spatial location where the corresponding transfer functions where computed.

In the transfer function analysis block 802, properties of the transfer functions $H_{ji}$ between adjacent regions could also be obtained by fitting a parametric model to $H_{ji}(\theta)$ in the frequency domain. For example, in the block 802, it may be assumed that the transfer function model as a function of the Lapace variable s has the form $$\hat{H}_{ji}(C, D, E, F, G)(s) = \frac{Cs^2 + D}{Es^2 + Fs + G} \quad (22)$$

The values of the parameters C,D,E,F,G could be obtained by minimizing some error between the measured transfer function and the model, for example a quadratic error over the frequency domain or maximum error over the frequency domain. More specifically, with a frequency weighting function W (ω) one may solve a minimization such as $$\min_{C,D,E,F,G} \max_{\omega \in [0,\Omega]} \left| [H_{ji}(j\omega) - \hat{H}_{ji}(C, D, E, F, G)(j\omega)]W(\omega) \right| \quad (23)$$

One or several of the parameters C,D,E,F,G or a function of these parameters may be displayed at a location collocated with the spatial location where the corresponding transfer functions where computed.

It should be clear to those skilled in the art that, while the description above used tissue displacements of adjacent tissue regions to compute transfer functions and coherence functions, tissue velocities could be used in a similar manner.

Structured Transfer Function Approach

In another embodiment of the invention, the parameters of the transfer function between adjacent regions of tissue could be directly determined from an implied local tissue model. This approach combines the transfer function view just discussed with the a-priori parametric model approach discussed above. The advantage of this approach is that significant parametric detail that correlates to tissue property can be obtained by using local information. This method will be illustrated by assuming a model for the discrete-time equivalent of the transfer function $H_{ji}$ between tissue input region i and tissue output region j. Let the dynamic interaction between the regions i and j be described by an autogregressive moving average (ARMA) model of order k as follows:

$$x_j(t) + a_1 x_j(t-\Delta) + a_2 x_j(t-2\Delta) + \ldots + a_k x_j(t-k\Delta) = c_0 x_i(t) + c_1 x_i(t-\Delta) + \ldots + c_k x_i(t-k\Delta) \quad (24)$$

where $\Delta$ is the sampling time and $\theta^T_{ji} = [a_1, a_2, \ldots, a_k, c_0, c_1, \ldots, c_k]$ is a vector of ARMA model parameters. If certain persistency of excitation conditions are met (again, these depend on how rich is the frequency content of the tissue excitation), then the parameters $a_1, a_2, \ldots, a_k$ and $c_0, c_1, \ldots, c_k$ can be identified by a number of techniques as found in L. Ljung, "System Identification, Theory For The User", Prentice Hall, 1999, including with the least-squares, recursive least-squares, instrumental variable, maximum likelihood and other techniques.

Figure 12:
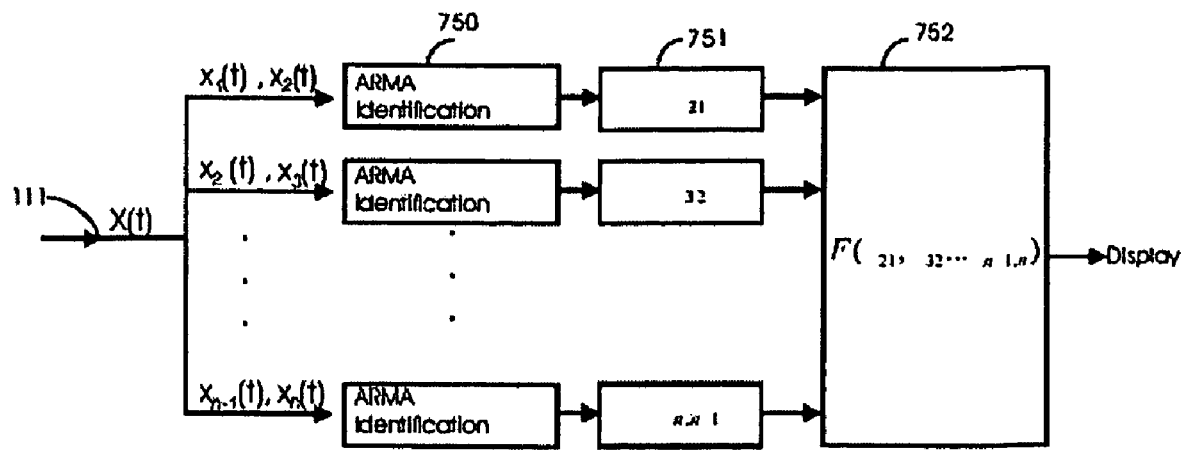
FIG. 12 shows the steps for transfer function modelling using the auto-regressive-moving-average model.

A subset of these parameters, or a computed function of these parameters can be displayed. See FIG. 12. In particular, note that if a second order transfer function is assumed between the input and output tissue regions i and j, respectively, then spring and damping values can be obtained from which tissue stiffness and viscosity can be determined.

The structured transfer function identification approach described above is summarized in FIG. 12. As before, a tissue displacement at a number of locations 111 is measured. Pairs of adjacent tissue displacement time sequences 703 are used as the inputs and outputs of ARMA models in signal processing blocks 750 to determine parameter values 751. The resulting parameter values, or functions of those parameters, are processed for display by another signal processing block 752.

It should be clear to the skilled in the art that, while the description above used tissue displacements of adjacent tissue regions to compute the parameters in the ARMA models, tissue velocities could be used in a similar manner.

Data Display

Several approaches have been described to determine mechanical properties of tissue that result from measurements of tissue displacements and/or velocities over a region of tissue. The tissue parameters are computed over an entire region of tissue, and the values of these parameters can be displayed at their correct spatial location in many ways. For example, in ultrasound imaging, elastography results may be displayed by superimposing a color map against a conventional ultrasound image. The conventional ultrasound image shows the spatial location to the examiner, while the superimposed color gives an idea of deviations of a parameter values away from an average for the image. It is also possible to display an additional image, for example a grey scale image, with grey scale values that are related (for example proportional, or inversely proportional through either linear or nonlinear transformations) to the parameter value at each spatial location.

EXAMPLES OF CALCULATED TISSUE PROPERTIES

For illustrative purposes, a few examples of calculated tissue properties (using one of the parameter identification methods described earlier) are given in FIGS. 13, 14, 15, 16.

Figure 13:
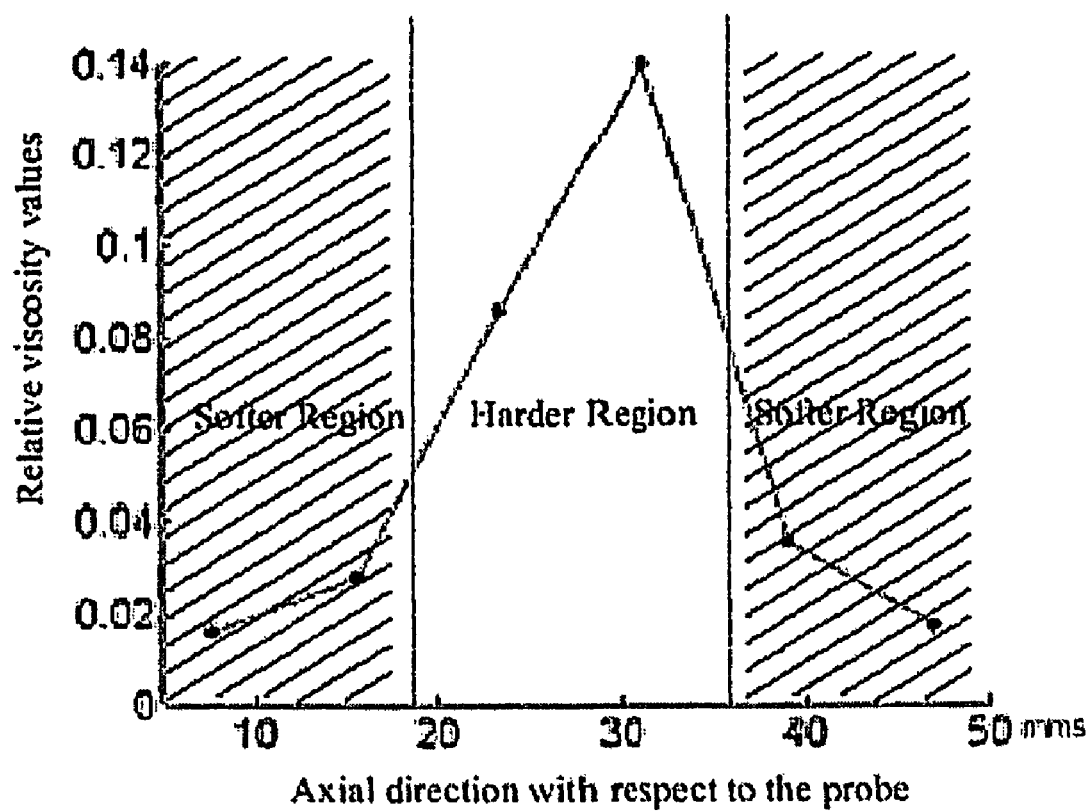
FIG. 13 shows a plot of viscosity versus depth of a layered artificial tissue sample obtained experimentally by parameter identification.

FIG. 13 shows the viscosity versus depth plot for a layered artificial tissue sample consisting of a hard layer between two soft layers. The calculation of the viscosity is done by excitation of the tissue sample with multiple frequency components, and measurement with ultrasound B-scans. The chosen model is one-dimensional with six elements connected by a parallel combination of a spring and damper, as shown in FIG. 8. The shaded areas represent the true separations between the hard and soft layers.

Figure 14:
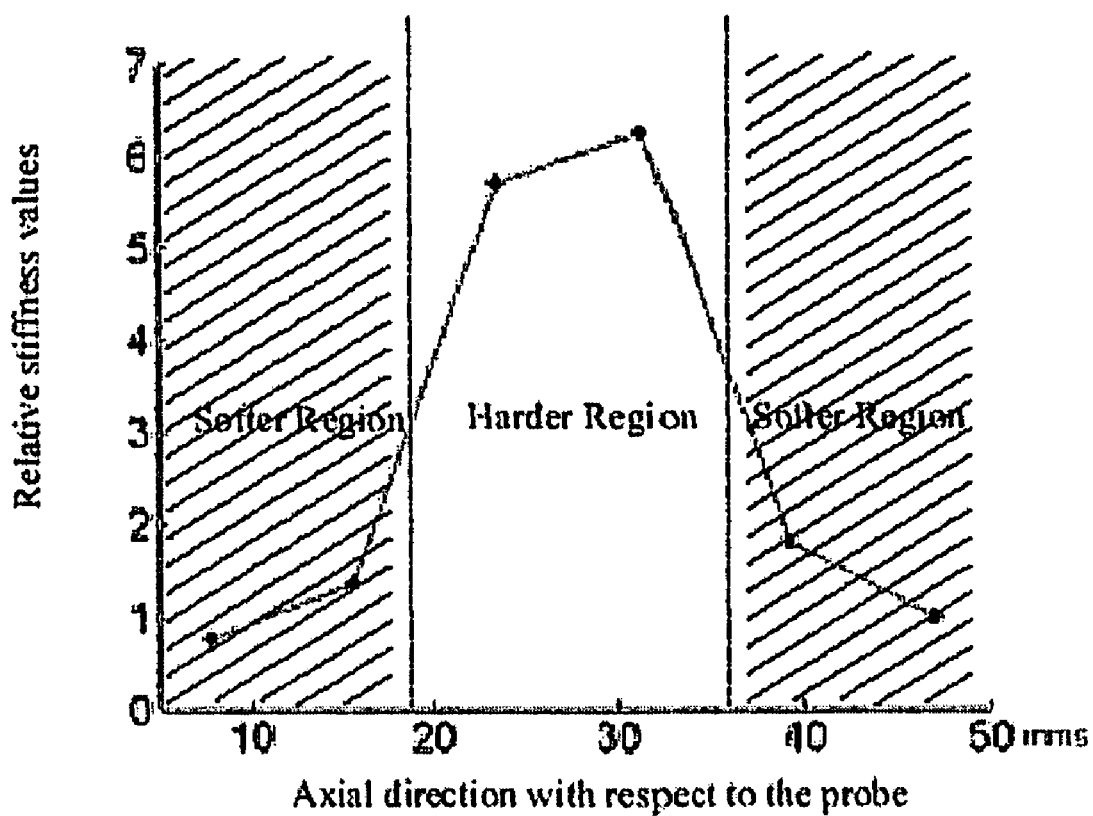
FIG. 14 shows a plot of stiffness versus depth of a layered artificial tissue sample obtained experimentally by parameter identification.
Figure 15:
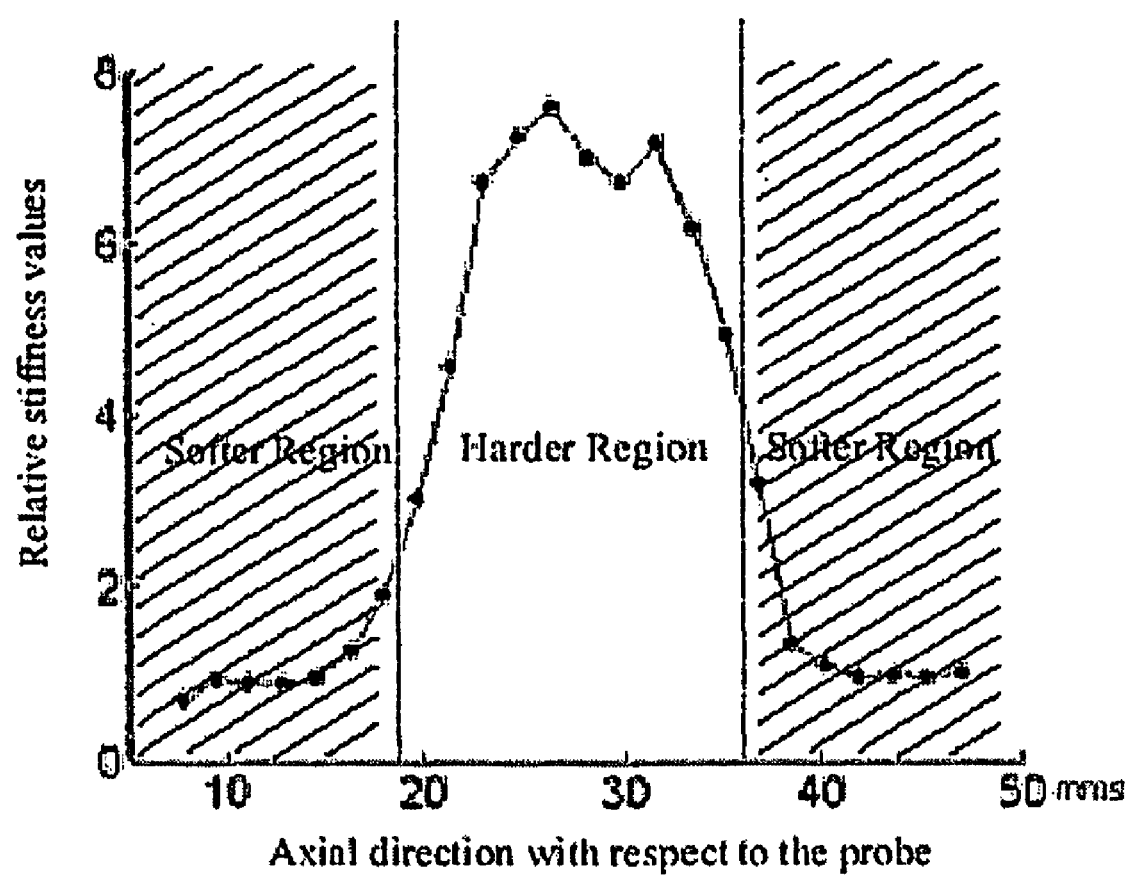
FIG. 15 shows a plot of stiffness versus depth of a layered artificial tissue sample obtained experimentally by the transfer function approach.

FIG. 14 shows the stiffness versus depth plot using the same approach as in FIG. 13. FIG. 15 shows the stiffness versus depth plot using the same excitation and artificial tissue sample, but now calculated using an unstructured transfer function approach. The analysis is done using a similar one-dimensional tissue model, but with twenty-six elements.

Figure 16:
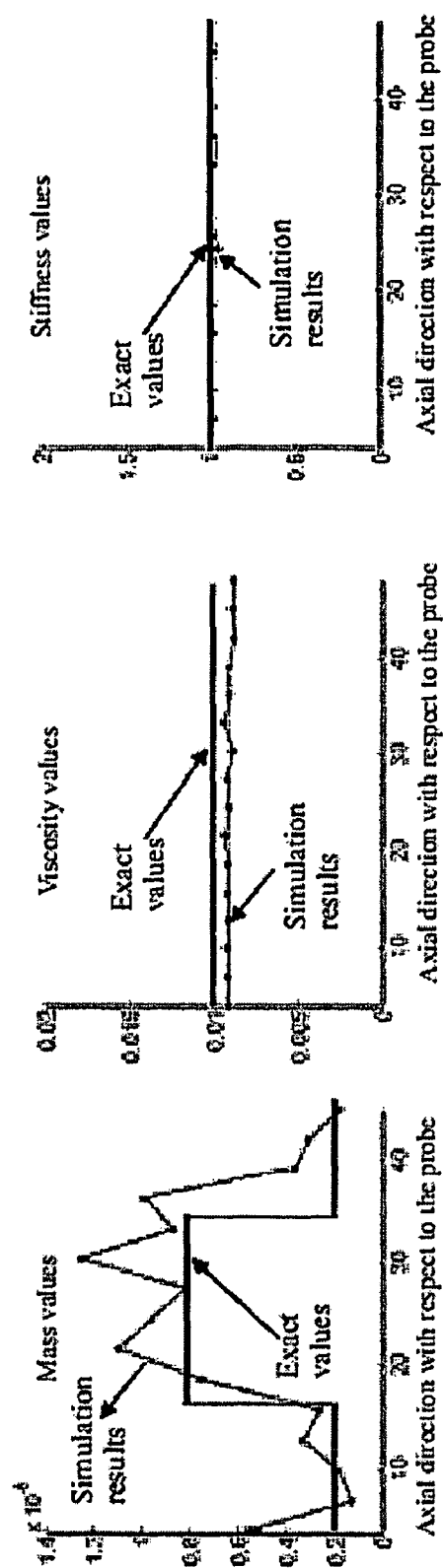
FIG. 16 shows results from simulations where mass, viscosity and stiffness are calculated by parameter identification.

FIG. 16 shows results from simulations where mass, viscosity and stiffness are calculated from a simulated three-layer tissue sample. An excitation with multiple frequencies is used together with a one-dimensional scattered distribution of ultrasound reflectors. A one-dimensional ultrasound transducer is also simulated to produce the measurements of the resulting motions of the reflectors. Again a similar one-dimensional mass-spring-damper model is used for modelling the measurements, but this time with 16 mass elements. The obtained stiffness viscosity, and mass distribution along the phantom is plotted together with the true values for comparison.

Figure 17:
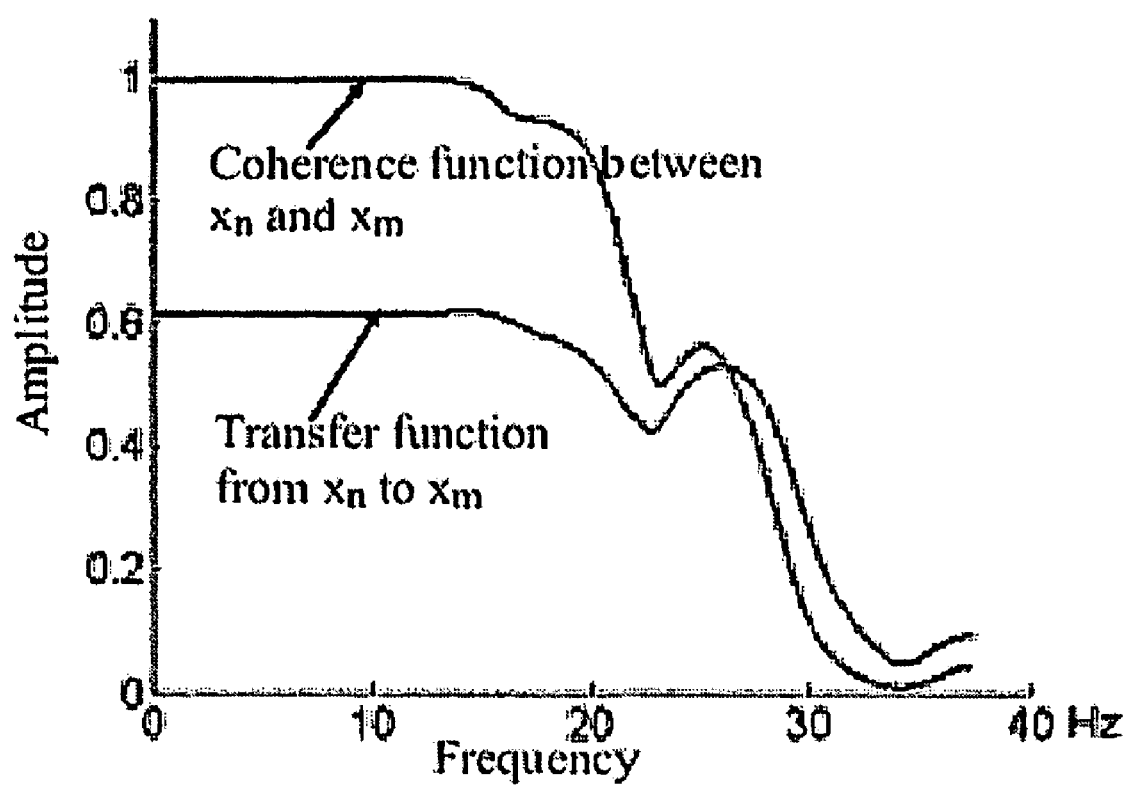
FIG. 17 shows experimental results for the calculated transfer function and coherence function for an artificial tissue sample.

Finally, FIG. 17 shows the typical shape of a transfer function and a coherence function for experimental data on an artificial tissue sample. The coherence function is unity for low frequencies which validates the assumption of linearity for the tissue in the frequency and excitation ranges used for calculating the results of FIG. 15.

Certain implementations of the invention comprise computer processors which execute software instructions which cause the processors to perform a method of the invention. For example, one or more processors in an ultrasound system may implement a method described herein by executing software instructions in a program memory accessible to the processors. The invention may also be provided in the form of a program product. The program product may comprise any medium which carries a set of computer-readable signals comprising instructions which, when executed by a computer processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like or transmission-type media such as digital or analog communication links.

Where a component (e.g. a software module, processor, assembly, device, circuit, vibrator etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method for determining localized properties within a region under study, the method comprising:
   applying a vibration signal to the region, the vibration signal simultaneously vibrating a plurality of locations within the region and having components at a plurality of frequencies;
   concurrently measuring a response to the vibration signal at each of the plurality of locations within the region at each of a plurality of times; and,
   from the measured responses determining localized properties of the region;
   wherein determining localized properties of the region comprises providing a parametric model of the region and estimating parameters of the parametric model for which the vibration signal would yield the measured responses.

2. A method according to claim 1 wherein the parametric model comprises a one-dimensional chain of linear dynamic systems.

3. A method according to claim 2 wherein the linear dynamic systems each comprise a mass connected to masses of one or more other ones of the linear dynamic systems by a spring and a damper arranged in parallel.

4. A method for determining localized properties within a region under study, the method comprising:
   applying a vibration signal to the region under study, the vibration signal simultaneously vibrating a plurality of locations within the region, and having components at a plurality of frequencies;
   concurrently measuring a response to the vibration signal at each of the plurality of locations at each of a plurality of times; and,
   from the measured responses determining localized properties of the region wherein determining localized properties of the region comprises determining transfer functions for portions of the region located between the plurality of locations.

5. A method according to claim 4 comprising fitting a parametric model to the transfer functions.

6. A method according to claim 1 comprising displaying an image based on the localized properties of the region.

7. A method according to claim 6 wherein the image based on the localized properties of the region is superimposed on a second image of the region.

8. A method according to claim 7 wherein the second image comprises an ultrasound image.

9. A method according to claim 7 wherein the second image comprises a computerized tomography image.

10. A method according to claim 1 wherein the region comprises tissue of a human or animal.

11. A method according to claim 10 wherein the region comprises a region within a human breast.

12. An imaging device comprising:
   a vibrator;
   a driver circuit connected to drive the vibrator to generate a vibration signal having components at a plurality of frequencies, the vibration signal capable of simultaneously vibrating a plurality of locations in a region of tissue;
   an imaging system disposed to measure responses comprising at least one of: a tissue displacement, a tissue velocity and a tissue acceleration at the plurality of locations at a plurality of times; and,
   a data processor connected to receive response data representing the responses, the data processor programmed to compute from the response data localized properties of the region by a process comprising estimating parameters of a parametric model of the region for which the vibration signal would yield the responses at the locations.

13. A method according to claim 1 wherein the response to the vibration signal comprises a time-varying displacement of the location.

14. A method according to claim 1 wherein the response to the vibration signal comprises one or more of displacement, velocity and acceleration of the location.

15. A method according to claim 1 wherein the parametric model models a plurality of masses coupled to one another by one or more viscoelastic couplings, each viscoelastic coupling comprising at least one of: a spring and a damper; wherein the estimated parameters of the parametric model comprise one or more of: a parameter corresponding to a mass of one of the plurality of masses; a parameter corresponding to a spring in one of the viscoelastic couplings, and a parameter corresponding to a damper of one of the viscoelastic couplings.

16. A method according to claim 1 wherein estimating parameters of the parametric model comprises arranging the measured responses to provide an overconstrained system of linear equations and computing an approximate solution to the system of linear equations.

17. A method according to claim 1 comprising determining image values for locations in an image based at least in part on the estimated parameters.

18. A method according to claim 17 comprising superimposing the image on an ultrasound image of the region.

19. A method according to claim 1 wherein the parametric model comprises a chain of linear dynamic systems.

20. A method according to claim 4 wherein determining the transfer functions for portions of the region comprises taking a first one of the plurality of locations to be an input of a linear dynamic system and a second one of the plurality of locations to be an output of the linear dynamic system and, from the responses corresponding to the first and second locations, calculating a corresponding transfer function.

21. A method according to claim 20 comprising, after determining the transfer functions, determining one or more properties of each of the transfer functions.

22. A method according to claim 4 wherein the properties comprise low-frequency magnitudes of the transfer functions.

23. A method according to claim 4 wherein the properties comprise averages of the magnitudes of the transfer functions at frequencies within a frequency range.

24. A method according to claim 4 comprising fitting a parametric model to the transfer functions in the frequency domain.

25. A method according to claim 4 comprising computing a coherence function corresponding to one or more of the transfer functions.

26. A method according to claim 5 comprising determining image values for locations in an image based at least in part on values of one or more parameters of the parametric model.

27. A method according to claim 4 comprising determining image values for locations in an image based at least in part on the localized properties of the region.

28. An imaging device according to claim 12 comprising:
 a needle having a proximal end coupled to the vibrator and a distal end that is insertable into the region.

29. An imaging device according to claim 28 wherein the needle comprises a cannula and a stylet extending through a bore of the cannula wherein the stylet is coupled to carry the vibration signal from the vibrator to a distal tip of the stylet.

30. An imaging device according to claim 12 wherein the vibrator is connected to deliver the vibration signal by way of a support structure capable of supporting a human subject.

31. An imaging device according to claim 12 wherein the imaging system comprises an ultrasound imaging system.

32. An imaging device according to claim 30 wherein the ultrasound imaging system comprises an ultrasound probe, the vibrator comprises a first vibrator mounted on the probe, and the imaging device comprises one or more additional vibrators mounted on the probe to cancel vibrations of the probe caused by the first vibrator.

33. An imaging device according to claim 32 comprising a vibration detector disposed to measure residual vibration of the ultrasound probe and a controller configured to drive one or more of the first and second vibrators based on a feedback signal from the vibration detector to reduce vibration of the ultrasound probe.

34. An imaging device according to claim 31 wherein the ultrasound imaging system comprises an ultrasound probe with the vibrator mounted on the probe, and the imaging device comprises means for cancelling vibrations of the probe caused by the vibrator.

* * * * *